United States Patent
Ohuchi et al.

(10) Patent No.: US 9,717,474 B2
(45) Date of Patent: Aug. 1, 2017

(54) IMAGE PROCESSING APPARATUS, ULTRASOUND DIAGNOSIS APPARATUS, AND IMAGE PROCESSING METHOD

(71) Applicant: Toshiba Medical Systems Corporation, Otawara (JP)

(72) Inventors: Hiroyuki Ohuchi, Otawara (JP); Shinichi Hashimoto, Otawara (JP); Yasuhiko Abe, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 286 days.

(21) Appl. No.: 14/557,622

(22) Filed: Dec. 2, 2014

(65) Prior Publication Data

US 2015/0173707 A1  Jun. 25, 2015

(30) Foreign Application Priority Data

Dec. 20, 2013  (JP) .................... 2013-264163

(51) Int. Cl.
 *A61B 8/08*  (2006.01)
 *A61B 8/00*  (2006.01)
 (Continued)

(52) U.S. Cl.
 CPC ............ *A61B 8/0883* (2013.01); *A61B 6/504* (2013.01); *A61B 8/463* (2013.01); *A61B 8/483* (2013.01);
 (Continued)

(58) Field of Classification Search
 CPC ......... A61B 6/503; A61B 6/5247; G06T 7/00; G06T 15/08
 See application file for complete search history.

(56) References Cited

U.S. PATENT DOCUMENTS

| | | | |
|---|---|---|---|
| 2005/0096522 A1* | 5/2005 | Reddy | A61B 6/032 600/407 |
| 2006/0239524 A1* | 10/2006 | Desh | G06F 19/321 382/128 |
| 2009/0043200 A1 | 2/2009 | Abe | |
| 2009/0096787 A1* | 4/2009 | Masumoto | G06T 7/0012 345/424 |
| 2009/0156933 A1* | 6/2009 | Gerard | G06T 7/0038 600/443 |

(Continued)

FOREIGN PATENT DOCUMENTS

JP  2009-39429  2/2009

OTHER PUBLICATIONS

Maurice Termeer et al. "Patient-Specific Mappings between Myocardial and Coronary Anatomy", Scientific Visualization; Advanced Concepts, 2010, 14 pages.

*Primary Examiner* — Jacinta M Crawford
*Assistant Examiner* — Jitesh Patel
(74) *Attorney, Agent, or Firm* — Oblon, McClelland, Maier & Neustadt, L.L.P.

(57) ABSTRACT

An image processing apparatus of an embodiment includes a combined image generator and a controller. The combined image generator projects, on three-dimensional data indicating three-dimensional heart function information obtained from a first volume data group obtained by imaging the heart of a subject, a three-dimensional shape of blood vessels nourishing a cardiac muscle included in second volume data obtained by imaging the heart, thereby producing three-dimensional combined data, and produces combined image data in which the three-dimensional combined data is developed on a surface. The controller causes a display unit to display the combined image data.

19 Claims, 16 Drawing Sheets

(51) Int. Cl.
  *G09G 5/377* (2006.01)
  *G09G 5/00* (2006.01)
  *G06T 19/20* (2011.01)
  *G06T 15/08* (2011.01)
  *A61B 6/03* (2006.01)
  *A61B 6/00* (2006.01)

(52) U.S. Cl.
  CPC ............ *A61B 8/5261* (2013.01); *G06T 19/20* (2013.01); *G09G 5/001* (2013.01); *G09G 5/377* (2013.01); *A61B 6/032* (2013.01); *A61B 6/481* (2013.01); *A61B 6/5247* (2013.01); *A61B 8/0891* (2013.01); *A61B 8/485* (2013.01); *A61B 8/488* (2013.01); *A61B 8/523* (2013.01); *A61B 8/543* (2013.01); *G06T 2210/41* (2013.01); *G06T 2219/2012* (2013.01); *G09G 2340/10* (2013.01)

(56) References Cited

U.S. PATENT DOCUMENTS

| | | | |
|---|---|---|---|
| 2009/0177089 A1* | 7/2009 | Govari | A61B 8/12 600/453 |
| 2009/0295802 A1* | 12/2009 | Kushwaha | G06T 15/08 345/424 |
| 2010/0074487 A1* | 3/2010 | Miyamoto | A61B 6/503 382/128 |
| 2010/0201687 A1* | 8/2010 | Breeuwer | G06T 15/08 345/424 |
| 2010/0274132 A1* | 10/2010 | Kim | A61B 8/483 600/443 |
| 2011/0190633 A1* | 8/2011 | Kawagishi | A61B 8/08 600/443 |
| 2013/0245473 A1* | 9/2013 | Ramanathan | A61B 5/0402 600/509 |

* cited by examiner

FIG.6
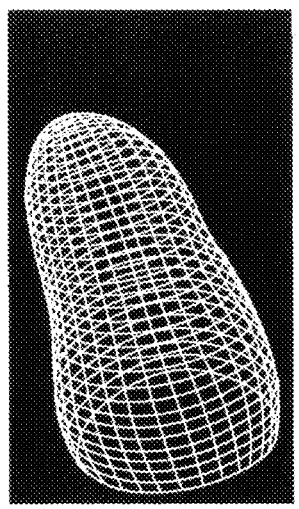
FIRST FRAME
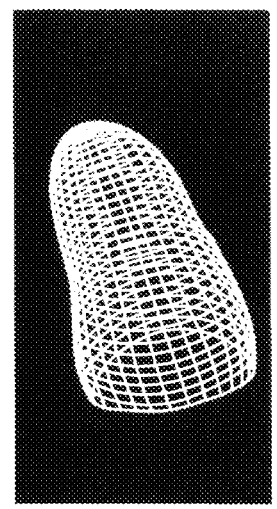
NTH FRAME
FIG.7
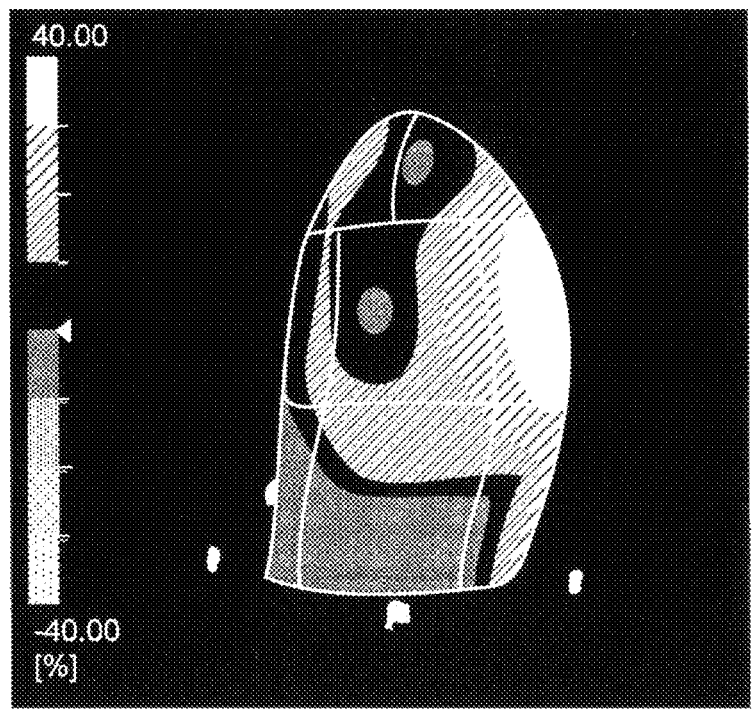

IMAGE PROCESSING APPARATUS, ULTRASOUND DIAGNOSIS APPARATUS, AND IMAGE PROCESSING METHOD

CROSS-REFERENCE TO RELATED APPLICATIONS

This application is based upon and claims the benefit of priority from Japanese Patent Application No. 2013-264163, filed on Dec. 20, 2013, the entire contents of all of which are incorporated herein by reference.

FIELD

Embodiments described herein relate generally to an image processing apparatus, an ultrasound diagnosis apparatus, and an image processing method.

BACKGROUND

To support diagnosis of cardiac disease, three-dimensional data has been produced and displayed in which functional information about a cardiac muscle at respective positions in the cardiac muscle is three-dimensionally mapped. Such three-dimensional data is produced using volume data obtained by imaging the heart of a patient by a medical diagnostic imaging apparatus.

In addition, polar maps have been produced and displayed. The polar map can express all of the functional information included in the three-dimensional data in a single image. The polar map, which is also called a "bull's eye plot", is an image in which the three-dimensional data is developed on a plane. Specifically, the polar map is an image in which three-dimensional data of the functional information at each of a plurality of short-axis cross sections from a cardiac base to a cardiac apex is projected on a "circle the center of which corresponds to the cardiac apex and the periphery of which corresponds to the cardiac base".

For example, the three-dimensional data is a three-dimensional contrast enhanced image of the heart imaged in a late phase. The three-dimensional contrast enhanced image of the heart in the late phase is data indicating a survival rate of cardiac muscle cells because contrast media are accumulated in necrotic or ischemic cardiac muscle cells. Another example of the three-dimensional data is a three-dimensional perfusion image in which "index values indicating perfusion dynamics of blood in the cardiac muscle" calculated from time series data of the three-dimensional contrast enhanced image are mapped. The three-dimensional perfusion image is also data indicating the survival rate of the cardiac muscle cells.

In the diagnosis of cardiac disease, it is important to grasp a positional relation between the cardiac muscle and coronary arteries that nourish the cardiac muscle. The coronary arteries are arteries that supply bloodstream (oxygen) to the cardiac muscle. No blood is supplied from a portion where the coronary arteries are constricted or completely obstructed to the downstream cardiac muscle. As a result, a motion function of a heart wall deteriorates. A doctor thus needs to grasp the portion of the cardiac muscle where the motion function deteriorates and further the portion of the coronary artery dominating the portion of the cardiac muscle.

An apparatus has been developed that has a function to extract the coronary arteries from the three-dimensional contrast enhanced image in the artery phase by segmentation processing, produce and display a rendering image after performing rendering processing on the extracted coronary arteries, and produce and display a polar map from the three-dimensional shape of the extracted coronary arteries. A technique has been also proposed in which a polar map is produced and displayed in which a "three-dimensional contrast enhanced image in the late phase" and a "three-dimensional shape of the coronary arteries", which are obtained from a magnetic resonance imaging (MRI) apparatus, are developed on the same plane.

Recently, an apparatus has been developed that calculates wall motion information (e.g., strain and displacement) at respective positions in the cardiac muscle by speckle tracking using the time series data of the three-dimensional ultrasound image. The apparatus can produce a three-dimensional analysis image (also called "plastic bag") in which the calculated wall motion information is mapped on a surface rendering image of the cardiac muscle in colors in accordance with the values, and further can produce a polar map from the three-dimensional analysis image. The wall motion information obtained by echocardiography makes it possible to quantitatively analyze motion functions in respective regions of the cardiac muscle and to perform a diagnosis on heart function in more detail by comparing with the three-dimensional data indicating the survival rate of the cardiac muscle cells.

Conventionally, a doctor checks the constricted portion in the coronary arteries with reference to the rendering image or the polar map of the coronary arteries obtained by a contrast enhanced CT inspection and also checks the portion of the cardiac muscle where the motion function deteriorates from the polar map of the wall motion information obtained by the echocardiography. In this way, in the conventional technique, a doctor observes two images separately, and grasps a positional relation between the portion of the cardiac muscle where the motion function deteriorates and the constricted portion of the coronary artery.

BRIEF DESCRIPTION OF THE DRAWINGS

FIG. 6 is a second schematic diagram to explain the analyzer;

FIG. 7 is a third schematic diagram to explain the analyzer;

DETAILED DESCRIPTION

The following describes embodiments of an image processing apparatus in detail with reference to the accompanying drawings.

The image processing apparatus of the embodiments includes a combined image generator and a controller. The combined image generator projects, on three-dimensional data indicating three-dimensional heart function information obtained from a first volume data group obtained by imaging the heart of a subject, a three-dimensional shape of blood vessels nourishing a cardiac muscle included in second volume data obtained by imaging the heart, thereby producing three-dimensional combined data, and produces combined image data in which the three-dimensional combined data is developed on a surface. The controller causes a display unit to display the combined image data.

First Embodiment

Figure 1:
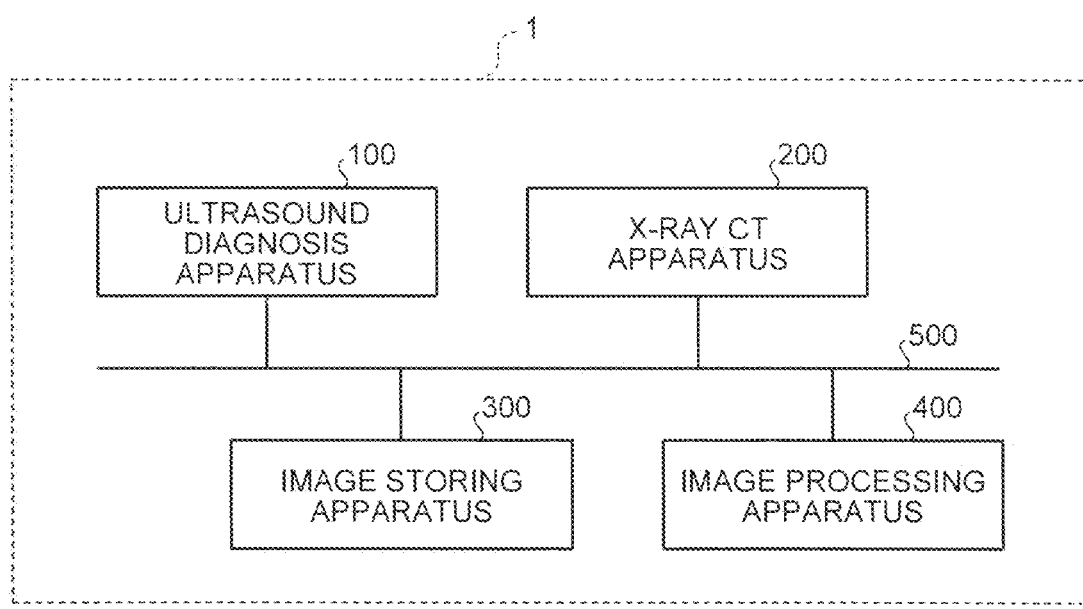
FIG. 1 is a schematic diagram illustrating a structural example of an image processing system in which an image processing apparatus according to a first embodiment is disposed.

The following describes a structural example of an image processing system in which the image processing apparatus according to a first embodiment is disposed. FIG. 1 is a schematic diagram illustrating a structural example of the image processing system in which the image processing apparatus according to the first embodiment is disposed.

As illustrated in FIG. 1, an image processing system 1 according to the first embodiment includes an ultrasound diagnosis apparatus 100, an X-ray computed tomography (CT) apparatus 200, an image storing apparatus 300, and an image processing apparatus 400. The respective apparatuses exemplarily illustrated in FIG. 1 can communicate directly or indirectly among them via an in-hospital local area network (LAN) 500 installed in a hospital, for example. For example, when a picture archiving and communication system (PACS) is introduced, the respective apparatuses transmit and receive medical images among them in conformity with the Digital Imaging and Communications in Medicine (DICOM) standard.

The respective apparatuses exemplarily illustrated in FIG. 1 each can read or display the data received from the other apparatuses as a result of transmitting or receiving data compliant with the DICOM standard. In the embodiment, data compliant with any standard may be transmitted and received as long as each apparatus can process the data received from the other apparatuses.

The ultrasound diagnosis apparatus 100 produces ultrasound image data of any cross section by an operator who adjusts a position of an ultrasound probe that performs two-dimensional ultrasound scanning. The ultrasound diagnosis apparatus 100 performs three-dimensional ultrasound scanning using a mechanical four-dimensional (4D) probe or a two-dimensional (2D) array probe to produce three-dimensional ultrasound image data (ultrasound volume data).

The X-ray CT apparatus 200 has a rotating frame that can rotate while supporting an X-ray tube emitting X-rays and an X-ray detector detecting X-rays having passed through a subject at the respective positions where the X-ray tube and the X-ray detector face each other. The X-ray CT apparatus 200 rotates the rotating frame while transmitting X-rays from the X-ray tube to collect data of X-rays after being transmitted, absorbed, and attenuated from all directions, and then reconstructs X-ray CT image data from the collected data. The X-ray CT image data indicates a cross-sectional image in a plane of rotation of the X-ray tube and the X-ray detector (in an axial plane). The X-ray detector includes a plurality of rows of detection elements, serving as X-ray detection elements, arranged in a channel direction. The rows are arranged along the body axis direction of a subject. For example, the X-ray CT apparatus 200 including the X-ray detector having 16 rows of the detection elements reconstructs a plurality of pieces (e.g., 16 pieces) of X-ray CT image data along the body direction of a subject from projection data collected as a result of one rotation of the rotating frame.

The X-ray CT apparatus 200 can reconstruct 500 pieces of X-ray CT image data covering the whole of a heart as three-dimensional X-ray CT image data (X-ray CT volume data) by helical scanning, in which the rotating frame is rotated and a couchtop with a subject placed thereon is moved, for example. For another example, the X-ray CT apparatus 200 including the X-ray detector having 320 rows of the detection elements can reconstruct the three-dimensional X-ray CT image data (X-ray CT volume data) covering the whole of a heart by conventional scanning, in which the rotating frame is rotated only one rotation. The X-ray CT apparatus 200 can take the three-dimensional X-ray CT image data (X-ray CT volume data) in a time-series manner by continuously performing the helical scanning or the conventional scanning. The ultrasound diagnosis apparatus 100 and the X-ray CT apparatus 200 according to the first embodiment are described in detail later.

The image storing apparatus 300 is a database that stores therein medical image data. Specifically, the image storing apparatus 300 puts medical image data transmitted from the ultrasound diagnosis apparatus 100 and the X-ray CT apparatus 200 in a storage of the image storing apparatus 300 and stores the data in the storage. The medical image data is stored in the image storing apparatus 300 in such a manner that the data and supplementary information such as a patient ID, an inspection ID, an apparatus ID, and a series ID in association with one another, for example.

The image processing apparatus 400 is a work station or a personal computer (PC), which is used by doctors and laboratory technicians who work in a hospital for interpretation of medical images, for example. Operators of the image processing apparatus 400 can acquire necessary medical image data from the image storing apparatus 300 by performing searches using the patient IDs, the inspection IDs, the apparatus IDs, and the series IDs, for example. The image processing apparatus 400 may receive the image data directly from the ultrasound diagnosis apparatus 100 and the X-ray CT apparatus 200. The image processing apparatus 400 can perform various types of image processing on the medical image data besides the display of the medical images for interpretation.

The following describes a case where the image processing apparatus 400 performs an image processing method according to the embodiment. Part or all of the various types of processing performed by the image processing apparatus 400 described below may also be performed by the ultrasound diagnosis apparatus 100 and the X-ray CT apparatus 200.

The image processing system 1 is not limited to being used when the PACS is introduced. The image processing system 1 is also applied to a case where an electronic health record system is introduced that manages electronic health records to which medical image data is attached, for example. In this case, the image storing apparatus 300 is a database that stores therein medical health records. The image processing system 1 is also applied to a case where a hospital information system (HIS) and a radiology information system (RIS) are introduced, for example. The image processing system 1 according to the embodiment may also include a magnetic resonance imaging (MRI) apparatus.

Figure 2:
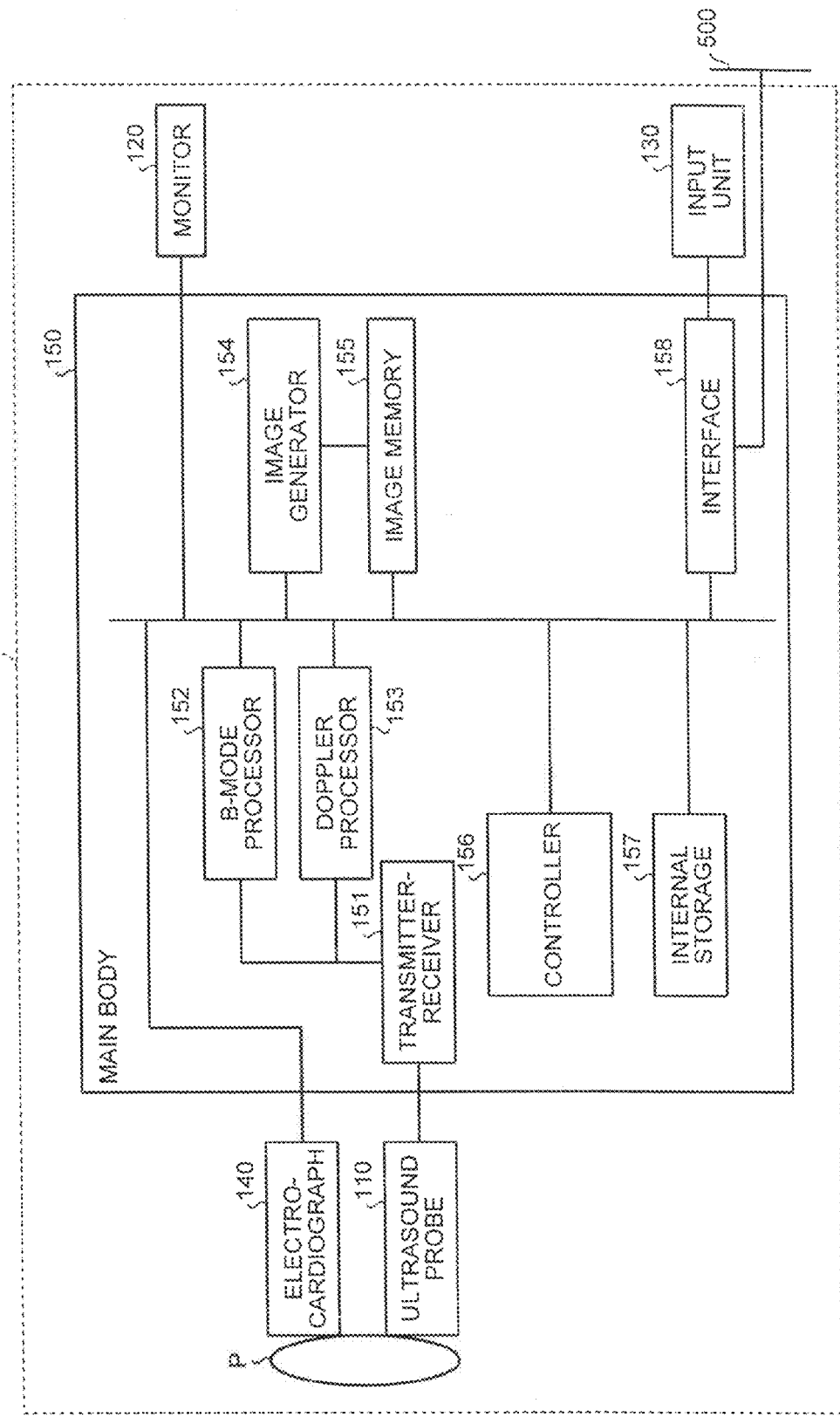
FIG. 2 is a block diagram illustrating an exemplary structure of an ultrasound diagnosis apparatus according to the first embodiment.

The following describes an exemplary structure of the ultrasound diagnosis apparatus 100 illustrated in FIG. 1 with reference to FIG. 2. FIG. 2 is a block diagram illustrating an exemplary structure of the ultrasound diagnosis apparatus according to the first embodiment. As exemplarily illustrated in FIG. 1, the ultrasound diagnosis apparatus 100 according to the first embodiment includes an ultrasound probe 110, a monitor 120, an input unit 130, an electrocardiograph 140, and a main body 150.

The ultrasound probe 110 transmits and receives ultrasound waves. The ultrasound probe 110 includes a plurality of transducer elements, which generate ultrasound waves on the basis of a drive signal supplied from a transmitter-receiver 151 included in the main body 150, which is described later, for example. The ultrasound probe 110 receives reflected waves from a subject P and converts the reflected waves into electrical signals. The ultrasound probe 110 includes a matching layer provided to the transducer elements and a backing material preventing ultrasound waves from propagating backward from the transducer elements, for example. The ultrasound probe 110 is connected to the main body 150 in a detachable manner.

Ultrasound waves transmitted from the ultrasound probe 110 to the subject P are reflected by a discontinuous surface of an acoustic impedance in body tissues of the subject P one after another, and received by the multiple transducer elements included in the ultrasound probe 110 as reflected wave signals. The amplitudes of the received reflected wave signals depend on differences in acoustic impedance of the discontinuous surfaces where ultrasound waves are reflected. The reflected wave signals of the transmitted ultrasound pulses reflected by moving bloodstream and a surface of a cardiac wall change in frequency depending on velocity components of the moving object in the ultrasound wave transmission direction by a Doppler effect.

The ultrasound probe 110 according to the first embodiment can scan the subject P with ultrasound waves two-dimensionally and three-dimensionally. Specifically, the ultrasound probe 110 according to the first embodiment scans the subject P with ultrasound waves two-dimensionally by the multiple transducer elements arranged in a row, and scans the subject P with ultrasound waves three-dimensionally by the multiple transducer elements swung at a certain angle (swing angle), i.e., the ultrasound probe 110 is a mechanical 4D probe. The ultrasound probe 110 according to the first embodiment is a 2D array probe that can scan the subject P with ultrasound waves three-dimensionally by the multiple transducer elements arranged in a matrix. The 2D array probe can also scan the subject P two-dimensionally by converging ultrasound waves and transmitting the converged ultrasound waves.

The input unit 130 includes a mouse, a keyboard, a button, a panel switch, a touch command screen, a foot switch, a trackball, and a joystick, for example. The input unit 130 receives various setting requests from an operator of the ultrasound diagnosis apparatus 100 and transfers the received various setting requests to the main body 150.

The monitor 120 displays a graphical user interface (GUI) allowing an operator of the ultrasound diagnosis apparatus 100 to input various setting requests using the input unit 130, and the ultrasound image data produced by the main body 150, for example.

The electrocardiograph 140 acquires an electrocardiogram (ECG) of the subject P as a biosignal of the subject P. The electrocardiograph 140 transmits the acquired electrocardiogram to the main body 150.

The main body 150 produces the ultrasound image data on the basis of the reflected wave signals received by the ultrasound probe 110. The main body 150 illustrated in FIG. 1 can produce the two-dimensional ultrasound image data on the basis of the two-dimensional reflected wave data received by the ultrasound probe 110. The main body 150 illustrated in FIG. 1 can produce the three-dimensional ultrasound image data (ultrasound volume data) on the basis of the three-dimensional reflected wave data received by the ultrasound probe 110.

As illustrated in FIG. 2, the main body 150 includes the transmitter-receiver 151, a B-mode processor 152, a Doppler processor 153, an image generator 154, an image memory 155, a controller 156, an internal storage 157, and an interface 158.

The transmitter-receiver 151 includes a pulse generator, a transmission delay unit, and a pulser, for example, and supplies the drive signal to the ultrasound probe 110. The pulse generator repeatedly generates, at a certain rate frequency, rate pulses for the formation of transmission ultrasound waves. The transmission delay unit provides, to each rate pulse generated by the pulse generator, a delay time for each transducer element necessary to converge ultrasound waves generated by the ultrasound probe 110 to a beam shape and to determine transmission directivity. The pulser applies drive signals (drive pulses) to the ultrasound probe 110 at timing based on the rate pulses. The transmission delay unit adjusts the transmission direction of ultrasound waves transmitted from the surfaces of the transducer elements to any direction by changing the delay time provided to each rate pulse.

The transmitter-receiver 151 has a function that can instantly change a transmission frequency and a transmission drive voltage for performing a certain scan sequence on the basis of an instruction from the controller 156, which is described later. Particularly, the change of the transmission drive voltage is achieved by a mechanism that electrically switches linear amplifier oscillation circuits that can instantly switch the voltage or a plurality of power source units.

The transmitter-receiver 151 includes a pre-amplifier, an analog to digital (A/D) converter, a reception delay unit, and an adder, for example. The transmitter-receiver 151 produces reflected wave data by performing various types of processing on the reflected wave signals received by the ultrasound probe 110. The pre-amplifier amplifies the reflected wave signal for each channel. The A/D converter A/D converts the amplified reflected wave signals. The reception delay unit provides the delay times necessary to determine the reception directivity. The adder produces the reflected wave data by performing adding processing on the reflected wave signals processed by the reception delay unit. The adding processing by the adder enhances the reflection components from the direction corresponding to the reception directivity of the reflected wave signals. As a result, an overall beam for the ultrasound wave transmission and reception is formed by the reception directivity and the transmission directivity.

The transmitter-receiver 151 causes the ultrasound probe 110 to transmit a two-dimensional ultrasound beam when the subject P is scanned two-dimensionally. The transmitter-receiver 151 produces the two-dimensional reflected wave data from the two-dimensional reflected wave signals received by the ultrasound probe 110. The transmitter-receiver 151 causes the ultrasound probe 110 to transmit a three-dimensional ultrasound beam when the subject P is scanned three-dimensionally. The transmitter-receiver 151 produces the three-dimensional reflected wave data from the three-dimensional reflected wave signals received by the ultrasound probe 110.

Various forms can be selected as the form of the output signal from the transmitter-receiver 151, such as a radio frequency (RF) signal, a signal called an in-phase-quadrature (IQ) signal including phase information, or a signal indicating amplitude information after envelope detection processing.

The B-mode processor 152 receives the reflected wave data from the transmitter-receiver 151 and performs logarithm amplification and the envelope detection processing on the reflected wave data to produce data (B-mode data) in which a signal intensity is expressed by luminance.

The Doppler processor 153 performs frequency analysis on velocity information from the reflected wave data received from the transmitter-receiver 151, extracts bloodstream, tissues, and contrast media echo components by the Doppler effect, and produces data (Doppler data) based on moving object information such as the velocity, the distribution, and the power, extracted at multiple points.

The B-mode processor 152 and the Doppler processor 153 according to the first embodiment can process both of the two-dimensional reflected wave data and the three-dimensional reflected wave data. Specifically, the B-mode processor 152 produces two-dimensional B-mode data from the two-dimensional reflected wave data and produces three-dimensional B-mode data from the three-dimensional reflected wave data. The Doppler processor 153 produces the two-dimensional Doppler data from the two-dimensional reflected wave data and produces the three-dimensional Doppler data from the three-dimensional reflected wave.

The image generator 154 produces the ultrasound image data from the data produced by the B-mode processor 152 and the Doppler processor 153. Specifically, the image generator 154 produces two-dimensional B-mode image data in which an intensity of the reflected wave is expressed by luminance from the two-dimensional B-mode data produced by the B-mode processor 152. The image generator 154 produces two-dimensional Doppler image data indicating the moving object information from the two-dimensional Doppler data produced by the Doppler processor 153. The two-dimensional Doppler image data is a velocity image, a distribution image, a power image, or an image of the combination of these images.

The image generator 154 generally produces the ultrasound image data for display by converting (scan conversion) a scanning line signal string for ultrasound scanning into a scanning line signal string in a video format typified by a TV format. Specifically, the image generator 154 produces the ultrasound image data for display by coordinate conversion in accordance with the ultrasound scanning manner by the ultrasound probe 110. The image generator 154 performs various types of image processing beside the scan conversion. For example, the image generator 154 performs image processing (smoothing processing) in which an image of average luminance is reproduced using a plurality of image frames after scan conversion or image processing (edge enhancement processing) in which a differential filter is used in an image. The image generator 154 combines character information including various parameters, a scale, and a body mark, for example, with the ultrasound image data.

The B-mode data and the Doppler data are the ultrasound image data before the scan conversion processing. The data produced by the image generator 154 is the ultrasound data for display after the scan conversion processing. The B-mode data and the Doppler data are also called raw data.

Furthermore, the image generator 154 produces the three-dimensional B-mode image data by performing coordinate conversion on the three-dimensional B-mode data produced by the B-mode processor 152. The image generator 154 produces the three-dimensional Doppler image data by performing coordinate conversion on the three-dimensional Doppler data produced by the Doppler processor 153. In other words, the image generator 154 produces the "three-dimensional ultrasound image data (ultrasound volume data)" from the "three-dimensional B-mode image data and the three-dimensional Doppler image data".

Furthermore, the image generator 154 performs various types of rendering processing on the volume data for producing various types of two-dimensional image data used for displaying the ultrasound volume data on the monitor 120. One of the rendering processing performed by the image generator 154 is processing in which a multi planar reconstruction (MPR) image is produced from the volume data by an MPR technique. Examples of the rendering processing performed by the image generator 154 include processing in which curved MPR is performed on the volume data and processing in which maximum intensity projection is performed on the volume data. Another one of the rendering processing performed by the image generator 154 is volume rendering (VR) processing in which the two-dimensional image data is produced in which three-dimensional information is reflected. Still another one of the rendering processing performed by the image generator 154 is surface rendering (SR) processing in which SR image data is produced that three-dimensionally renders the shape of the surface of a rendering object.

The image memory 155 is a memory that stores therein the image data for display produced by the image generator 154. The image memory 155 can also store therein the data produced by the B-mode processor 152 and the Doppler processor 153. The B-mode data and the Doppler data stored by the image memory 155 can be called by an operator after a diagnosis, for example. The data is retrieved via the image generator 154 and served as the ultrasound image data for display.

The image generator 154 stores the ultrasound image data and a time at which the ultrasound scanning is performed for producing the ultrasound image data in the image memory 155 in association with an electrocardiogram transmitted from the electrocardiograph 140. The image processing apparatus 400, which is described later, can acquire a cardiac time phase at the ultrasound scanning performed for producing the ultrasound image data by referring to the data acquired from the image memory 155.

The internal storage 157 stores therein a control program for ultrasound transmission and reception, image processing, and display processing, diagnosis information (e.g., a patient ID, and a doctor's observation), and various types of data such as a diagnosis protocol and various body marks. The internal storage 157 is also used for storing the image data stored in the image memory 155, for example, as needed. The data stored in the internal storage 157 can be transferred to external apparatuses via the interface 158, which is described later. The data stored in external apparatuses can also be transferred to the internal storage 157 via the interface 158. Examples of the external apparatuses include the X-ray CT apparatus 200, the image storing apparatus 300, and the image processing apparatus 400, which are illustrated in FIG. 1.

The controller 156 controls the whole processing of the ultrasound diagnosis apparatus 100. Specifically, the controller 156 controls the processing of the transmitter-receiver 151, the B-mode processor 152, the Doppler processor 153, and the image generator 154 on the basis of the various setting requests input by the operator via the input unit 130, the various control programs and various types of data read from the internal storage 157. The controller 156 performs control such that the ultrasound image data for display stored in the image memory 155 and the internal storage 157 is displayed on the monitor 120.

The controller 156 outputs the data stored in the image memory 155 and the internal storage 157 to the external apparatuses via the interface 158, for example. For example, the controller 156 transfers, to the image processing apparatus 400, data in which a B-mode ultrasound volume data group obtained by ultrasound scanning the heart of the subject P three-dimensionally is associated with the electrocardiogram.

The interface 158 interfaces with the input unit 130, the in-hospital LAN 500, the X-ray CT apparatus 200, the image storing apparatus 300, and the image processing apparatus 400. For example, the various types of setting information and various instructions received by the input unit 130 from the operator are transferred to the controller 156 by the interface 158. For another example, the data output by the controller 156 for being transferred to the external apparatuses is transferred to the external apparatuses by the interface 158 via the in-hospital LAN 500. For still another example, the output data output by the X-ray CT apparatus 200 and the image processing apparatus 400 for being transferred is stored in the internal storage 157 via the interface 158.

Figure 3:
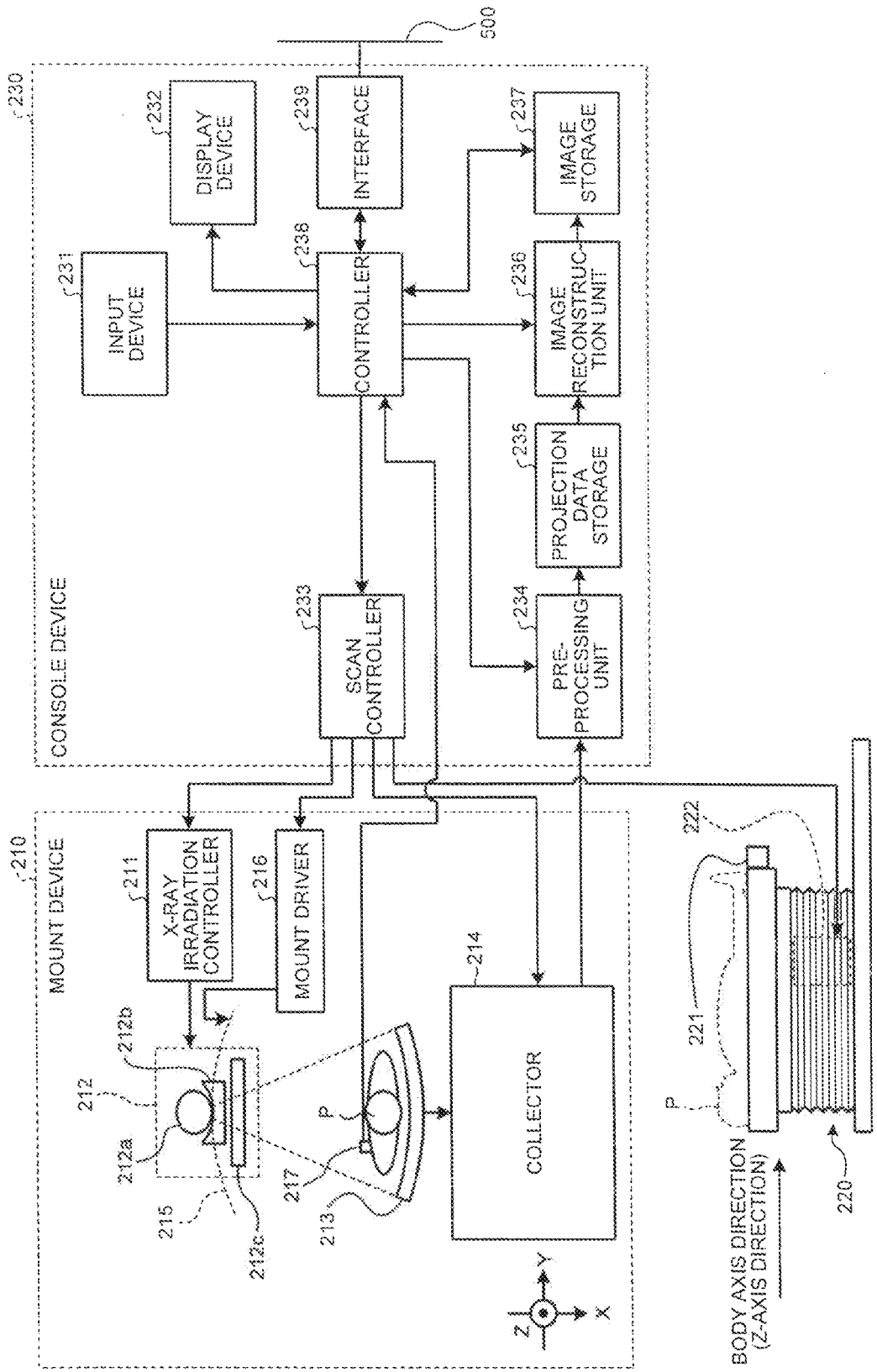
FIG. 3 is a block diagram illustrating an exemplary structure of an X-ray CT apparatus according to the first embodiment.

The following describes an exemplary structure of the X-ray CT apparatus 200 illustrated in FIG. 1 with reference to FIG. 3. FIG. 3 is a block diagram illustrating an exemplary structure of the X-ray CT apparatus according to the first embodiment. As illustrated in FIG. 3, the X-ray CT apparatus 200 according to the first embodiment includes a mount device 210, a couch device 220, and a console device 230.

The mount device 210 irradiates the subject P with X-rays and collects the projection data from the detection data of X-rays having passed through the subject P. The mount device 210 includes an X-ray irradiation controller 211, an X-ray generator 212, an X-ray detector 213, a collector 214, a rotating frame 215, a mount driver 216, and an electrocardiograph 217.

The rotating frame 215 supports the X-ray generator 212 and the X-ray detector 213 such that they can rotate around the subject P. The X-ray generator 212 includes an X-ray tube 212a, which is described later. The rotating frame 215 is an annular frame that supports the X-ray generator 212 and the X-ray detector 213 such that they face each other interposing the subject P and is rotated at a high speed on a circular path around the subject P as the center by the mount driver 216, which is described later.

The X-ray generator 212 generates X-rays and irradiates the subject P with the generated X-rays. The X-ray generator 212 includes the X-ray tube 212a, a wedge 212b, and a collimator 212c.

The X-ray tube 212a is a vacuum tube that generates X-ray beams by a high voltage supplied by the X-ray irradiation controller 211, which is described later, for irradiating the subject P, for example. The X-ray tube 212a emits X-ray beams to irradiate the subject P with the rotation of the rotating frame 215. The X-ray tube 212a generates X-ray beams widening with a fan angle and a corn angle.

The wedge 212b is an X-ray filter that regulates an amount of the X-rays emitted from the X-ray tube 212a. The collimator 212c is a slit that narrows the irradiation area of the X-rays the amount of which is regulated by the wedge 212b under the control of the X-ray irradiation controller 211, which is described later.

The X-ray irradiation controller 211 serves as a high voltage generator to supply a high voltage to the X-ray tube 212a. The X-ray tube 212a generates X-rays using the high voltage supplied from the X-ray irradiation controller 211. The X-ray irradiation controller 211 adjusts the amount of X-rays with which the subject P is irradiated by adjusting a tube voltage and a tube current supplied to the X-ray tube 212a. The X-ray irradiation controller 211 adjusts the irradiation area (the fan angle and the corn angle) of X-rays by adjusting an aperture of the collimator 212c.

The mount driver 216 drives the rotating frame 215 to rotate, thereby rotating the X-ray generator 212 and the X-ray detector 213 on a circular path around the subject P as the center.

The X-ray detector 213 detects X-rays that are emitted from the X-ray tube 212a and having passed through the subject P. Specifically, the X-ray detector 213 detects the X-rays that are emitted from the X-ray tube 212a and having passed through the subject P by the X-ray detection elements arranged two-dimensionally. The X-ray detector 213 illustrated in FIG. 3 is a two-dimensional array detector (plane detector) that outputs X-ray intensity distribution data indicating an intensity distribution of X-rays having passed through the subject P. In the X-ray detector 213, a plurality of X-ray detection elements (a row of the detection elements) are arranged in a channel direction (the Y-axis direction illustrated in FIG. 3) and a plurality of rows are arranged in the body axis direction of the subject P (the Z-axis direction illustrated in FIG. 3). For example, the X-ray detector 213 includes 320 rows of the detection elements arranged along the body axis direction of the subject P and detects the intensity distribution data of X-rays having passed through the subject P in a wide area.

The collector 214, which is a data acquisition system (DAS), collects the projection data from the detection data of X-rays detected by the X-ray detector 213. For example, the collector 214 performs amplification processing, A/D conversion processing, and sensitivity correction processing between channels on the X-ray intensity distribution data detected by the X-ray detector 213, thereby producing the projection data, and then transmits the produced projection data to the console device 230.

The electrocardiograph 217 acquires an electrocardiogram of the subject P as a biosignal of the subject P in the same manner as the electrocardiograph 140 illustrated in FIG. 2, and transmits the acquired electrocardiogram to the console device 230 (a controller 238).

The couch device 220, on which the subject P lays, includes a couchtop 221 and a couch driver 222. The couchtop 221 is a plate on which the subject P lays. The couch driver 222 moves the couchtop 221 in the Z-axis direction under the control of a scan controller 233, which is described later, thereby moving the subject P inside the rotating frame 215 (in an imaging space).

The mount device 210 performs helical scanning in which the rotating frame 215 is rotated while the couchtop 221 is moved so as to scan the subject P by a helical movement, for example. The mount device 210 performs conventional scanning in which the rotating frame 215 is rotated while the position of the subject P is fixed so as to scan the subject P on a circular path after the couchtop 221 is moved. The mount device 210 performs a step and shoot technique in which the conventional scan is performed in a plurality of scan areas while the position of the couchtop 221 is inched by a constant distance.

The console device 230 receives the operator's operation on the X-ray CT apparatus 200 and reconstructs the X-ray CT image data from the X-ray detection data collected by the mount device 210. The console device 230 includes an input device 231, a display device 232, the scan controller 233, a pre-processing unit 234, a projection data storage 235, an image reconstruction unit 236, an image storage 237, the controller 238, and an interface 239.

The input device 231 includes a mouse, a keyboard, a button, and a pedal (foot switch) that are used by the operator of the X-ray CT apparatus 200 to input various instructions and settings. The input device 231 transfers the instructions and information about settings received from the operator to the controller 238.

The display device 232, which is a monitor the operator refers to, displays the X-ray CT image data to the operator and a graphical user interface (GUI) for receiving various instructions and settings from the operator via the input device 231, under the control of the controller 238.

The scan controller 233 controls collection processing of the projection data by the mount device 210 by controlling the operation of the X-ray irradiation controller 211, the mount driver 216, the collector 214, and the couch driver 222 under the control of the controller 238, which is described later.

The pre-processing unit 234 performs the logarithmic conversion processing and correction processing such as offset correction, the sensitivity correction, and beam hardening correction on the projection data produced by the collector 214 to produce the corrected projection data. In the following description, the corrected projection data produced by the pre-processing unit 234 is simply described as the projection data. The projection data storage 235 stores therein the projection data produced by the pre-processing unit 234.

The image reconstruction unit 236 reconstructs the X-ray CT image data using the projection data stored by the projection data storage 235. Various techniques are available for the reconstruction. For example, inverse projection processing is available. One of the inverse projection processing is a filtered back projection (FBP) technique, for example. The image reconstruction unit 236 may reconstruct the X-ray CT image data using successive approximation.

The image reconstruction unit 236 can reconstruct the three-dimensional X-ray CT image data (X-ray CT volume data) using the projection data collected by the helical scanning, the conventional scanning using the X-ray detector 213 serving as the plane detector, or the conventional scanning of the step and shoot technique. The image reconstruction unit 236 produces the two-dimensional image data for display by performing the various types of rendering processing on the X-ray CT volume data. Examples of the rendering processing include the MPR processing, the MIP processing, the VR processing, and the SR processing, as described above.

The image storage 237 stores therein the various types of image data produced by the image reconstruction unit 236. For example, the image storage 237 stores therein the X-ray CT volume data of the heart of the subject P produced by the image reconstruction unit 236 and a time at which the CT scan is performed for producing the X-ray CT volume data in association with the electrocardiogram transmitted from the electrocardiograph 217. The image processing apparatus 400, which is described later, can acquire the cardiac time phase of the CT scan performed for producing the X-ray CT volume data of the heart of the subject P by referring to the data stored in the image storage 237.

The controller 238 controls the whole X-ray CT apparatus 200 by controlling the operation of the mount device 210, the couch device 220, and the console device 230. Specifically, the controller 238 controls the scan operation by the mount device 210 by controlling the scan controller 233. The controller 238 controls image reconstruction processing and image generation processing by the console device 230 by controlling the pre-processing unit 234 and the image reconstruction unit 236. The controller 238 performs control such that the various types of image data stored in the image storage 237 are displayed on the display device 232. The controller 238 outputs the various types of image data stored in the image storage 237 to the external apparatuses via the interface 239. For example, the controller 238 transfers, to the image processing apparatus 400, data in which the X-ray CT volume data group obtained by CT scan of the heart of the subject P three-dimensionally is associated with the electrocardiogram.

The interface 239 interfaces with the in-hospital LAN 500, the ultrasound diagnosis apparatus 100, the image storing apparatus 300, and the image processing apparatus 400. For example, the data output by the controller 238 for being transferred to the external apparatuses is transferred to the external apparatuses by the interface 239 via the in-hospital LAN 500. For another example, the output data output by the ultrasound diagnosis apparatus 100 and the image processing apparatus 400 for being transferred is stored in the image storage 237 via the interface 239.

Figure 4:
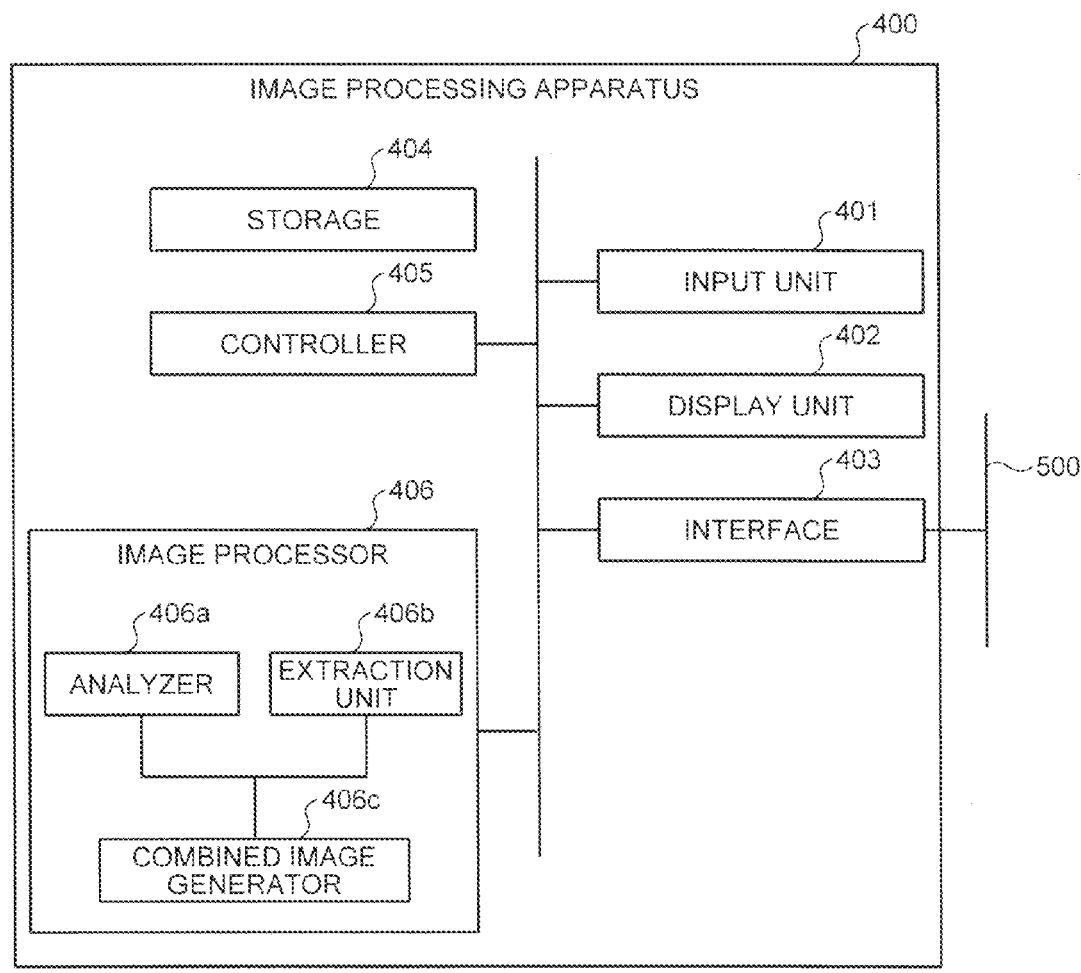
FIG. 4 is a block diagram illustrating an exemplary structure of the image processing apparatus according to the first embodiment.

The following describes an exemplary structure of the image processing apparatus 400 according to the first embodiment with reference to FIG. 4. FIG. 4 is a block diagram illustrating an exemplary structure of the image processing apparatus according to the first embodiment. As illustrated in FIG. 4, the image processing apparatus 400 according to the first embodiment includes an input unit 401, a display unit 402, an interface 403, a storage 404, a controller 405, and an image processor 406.

The input unit 401, which includes a mouse, a keyboard, and a trackball, receives input for various types of operation of the image processing apparatus 400 from the operator. Specifically, the input unit 401 according to the first embodiment receives input of information for acquiring the volume data to be subjected to the image processing from the ultrasound diagnosis apparatus 100, the X-ray CT apparatus 200, and the image storing apparatus 300, for example. For example, the input unit 401 receives inputs such as the patient ID, the inspection ID, and the series ID. The input unit 401 according to the first embodiment also receives input of conditions relating to the image processing.

The display unit 402 is a monitor, for example, and displays various types of information. Specifically, the display unit 402 according to the first embodiment displays a graphical user interface (GUI) for receiving various operations from the operator, the various types of image data acquired from the external apparatuses, and the results of the image processing performed by the image processing apparatus 400, for example.

The interface 403 communicates with other apparatuses. For example, the interface 403 transmits information such as the patient ID received by the input unit 401 to the ultrasound diagnosis apparatus 100, the X-ray CT apparatus 200, and the image storing apparatus 300, and receives medical image data to be subjected to the image processing from those external apparatuses.

The storage 404, which is a hard disk drive or a semiconductor memory, for example, stores therein various types of information. Specifically, the storage 404 stores therein the ultrasound volume data and the X-ray CT volume data acquired via the interface 403. The storage 404 according to the first embodiment stores therein data undergoing image processing or data after the image processing, for example.

The controller 405 is an electronic circuit such as a central processing unit (CPU) or a micro processing unit (MPU), or an integrated circuit such as an application specific integrated circuit (ASIC) or a field programmable gate array (FPGA), and controls the whole image processing apparatus 400.

For example, the controller 405 according to the first embodiment controls the display of the GUI and the resulting data of the image processing on the display unit 402. For another example, the controller 405 controls transmitting and receiving of the volume data between the image processing apparatus 400 and the external apparatuses via the interface 403. For still another example, the controller 405 controls the image processing performed by the image processor 406, which is described below. For still another example, the controller 405 controls reading of the volume data from the storage 404 and storing of data in the image processing and data after the image processing into the storage 404.

The image processor 406 performs various types of image processing for computer-aided diagnosis (CAD). As illustrated in FIG. 4, the image processor 406 according to the first embodiment includes an analyzer 406a, an extraction unit 406b, and a combined image generator 406c for performing various types of image processing on the volume data taken by the different types of medical image diagnostic apparatuses.

The analyzer 406a, the extraction unit 406b, and the combined image generator 406c perform the following processing, thereby producing a piece of image data that makes it possible to readily grasp a positional relation between a portion where heart function deteriorates and a portion causing the deterioration of the heart function.

The analyzer 406a acquires the three-dimensional heart function information from the first volume data group of the heart of the subject P, the heart being imaged by a first medical image diagnostic apparatus. The extraction unit 406b acquires the three-dimensional shape of blood vessels nourishing the cardiac muscle (i.e., coronary arteries) from the second volume data of the heart of the subject P, the heart being imaged by a second medical image diagnostic apparatus.

The combined image generator 406c produces combined image data in which the three-dimensional heart function information acquired by the analyzer 406a and the three-dimensional shape acquired by the extraction unit 406b are developed on a plane in a state where the three-dimensional heart function information and the three-dimensional shape are aligned with each other. Specifically, the combined image generator 406c aligns the volume data (hereinafter described as target volume data) obtained out of the first volume data group at the cardiac time phase substantially the same as the cardiac time phase at which the second volume data is acquired with the second volume data, and produces the combined image data on the basis of the alignment result.

The first volume data group is the ultrasound volume data group. In the embodiment, the B-mode ultrasound volume data group that the ultrasound diagnosis apparatus 100 produces in a time-series manner are used as the first volume data group. The three-dimensional heart function information is local motion information about a cardiac muscle obtained by tracking processing using the ultrasound volume data group. In the embodiment, the analyzer 406a calculates time series data of the local motion information about the cardiac muscle by the tracking processing using the ultrasound volume data group.

The second volume data is the X-ray CT volume data. The three-dimensional shape is the volume data of coronary arteries extracted from the X-ray CT volume data. In the embodiment, the X-ray CT volume data in a diastolic phase produced by the X-ray CT apparatus 200 is used as the second volume data, for example. In the embodiment, the extraction unit 406b produces coronary artery volume data in which a region of the coronary arteries is extracted by performing segmentation processing on the X-ray CT volume data in the diastolic phase. In the embodiment, a case is described where the X-ray CT volume data in an arterial phase where the coronary arteries are enhanced with contrast media in the diastolic phase is used in order to readily perform the segmentation processing. The embodiment can also be applied to a case where MRI volume data in the diastolic phase produced by an MRI apparatus is used as the second volume data.

The following describes an example of the processing performed by the analyzer 406a and the extraction unit 406b. Thereafter, an example of the processing is described that is performed by the combined image generator 406c according to the first embodiment.

The operator of the image processing apparatus 400 inputs the patient ID and the inspection ID of the subject P, which is a patient, using the input unit 401, for example. As a result, the controller 405 acquires the ultrasound volume data group (a plurality of pieces of ultrasound volume data in time series obtained by the B-bode imaging) of the imaged heart of the subject P from the ultrasound diagnosis apparatus 100 or the image storing apparatus 300 via the interface 403. The controller 405 acquires the X-ray CT volume data of the imaged heart of the subject P in the diastolic phase from the X-ray CT apparatus 200 or the image storing apparatus 300 via the interface 403.

Figure 5:
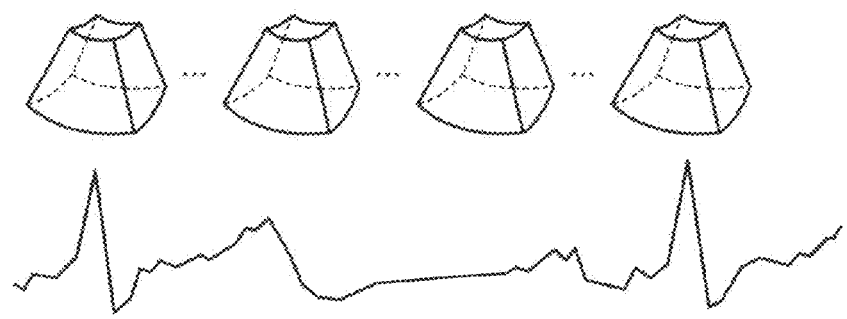
FIG. 5 is a first schematic diagram to explain an analyzer.

The controller 405 then stores the acquired ultrasound volume data group and X-ray CT volume data in the storage 404. The analyzer 406a performs the following processing under the control of the controller 405. FIGS. 5 to 7 are schematic diagrams to explain the analyzer.

As illustrated in FIG. 5, the analyzer 406a acquires, from the storage 404, a plurality of pieces of ultrasound volume data that corresponds to one or more heartbeats in chronological order and is associated with the electrocardiogram. Each ultrasound volume data includes the left ventricle of the subject P. The analyzer 406a analyzes the ultrasound volume data group illustrated in FIG. 5 and calculates time series data of the motion information at the respective points in the cardiac muscle of the left ventricle.

Specifically, the analyzer 406a calculates the motion information by processing including pattern matching between image data using the tracking results of a plurality of tracking points, which are described later. More specifically, the analyzer 406a calculates the motion information about the cardiac muscle (heart wall) using the result of three-dimensional speckle tracking (3D speckle tracking, hereinafter described as "3DT") performed on three-dimensional moving image data obtained by a three-dimensional echo technique. The speckle tracking technique is a technique that estimates the accurate movement using an optical flow technique or various types of spatiotemporal correction processing, for example, together with the pattern matching processing. The speckle tracking technique includes some techniques that estimate the movement without the pattern matching processing.

The input unit 401 receives, from the operator, a display request of a first frame (first volume) in the ultrasound volume data group, for example. The controller 405 to which the display request is transferred reads the ultrasound volume data of the first frame from the storage 404 and causes the display unit 402 to display the ultrasound volume data. The controller 405 then causes the analyzer 406a to produce a plurality of pieces of MPR image data of the cross sections of the ultrasound volume data of the first frame cut in a plurality of directions, and causes the display unit 402 to display the produced data. For example, the analyzer 406a produces the MPR image data of the multiple cross sections including the MPR image data of two cross sections corresponding to a two-chamber cross section and a four-chamber cross section.

The operator refers to the multiple pieces of MPR image data displayed on the display unit 402 and sets a plurality of tracking points for 3DT. For example, the operator traces the positions of the endocardium of the left ventricle and the epimyocardium in each MPR image data to designate the outline of the endocardium and the outline of the epimyocardium. The analyzer 406a structures a three-dimensional outline of the endocardium and a three-dimensional outline of the epimyocardium from the designated outline of the endocardium and the outline of the epimyocardium. The analyzer 406a sets the respective points constituting the three-dimensional outline of the endocardium of the first frame, which are exemplarily illustrated on the left in FIG. 5, as the tracking points. The analyzer 406a sets the respective points constituting the three-dimensional outline of the epimyocardium of the first frame (not illustrated) as the tracking points. The analyzer 406a sets template data for each of the tracking points set in the first frame. The template data is composed of a plurality of voxels each of which corresponds to the tracking point.

The analyzer 406a searches for a region most matching with the speckle pattern of the template data between two frames, thereby tracking to which position the template has moved in the next frame. As a result, the analyzer 406a tracks to which positions the respective positions of the first frame have moved in the nth frame, as illustrated on the right in FIG. 5. The mesh for setting the tracking points may be set by the analyzer 406a by detecting the endocardial surface and the epicardial surface of the left ventricle included in the first frame.

In this way, the analyzer 406a performs the 3DT on the ultrasound volume data group for the whole of the left ventricle (e.g., the endocardium and the epicardium of the left ventricle). The analyzer 406a produces the time series data of the motion information at the respective tracking points on the basis of the results of the 3DT. For example, the analyzer 406a calculates a strain as the motion information from the results of the 3DT of the endocardium and the epicardium. The analyzer 406a calculates a strain (LS) in a longitudinal direction, a strain (CS) in a circumferential direction, and a strain (RS) in a radial direction.

For another example, the analyzer 406a calculates an area change ratio (AC) of the endocardial surface of the left ventricle from the results of the 3DT of the endocardium. For still another example, the analyzer 406a may calculate a displacement from the results of the 3DT of the endocardium or the epicardium. When the displacement is used as the motion information, the analyzer 406a can calculate a displacement (LD) in the longitudinal direction and a displacement (RD) in a wall thickness direction. The analyzer 406a may calculate an absolute displacement (AD) of the tracking point at a time phase different from a reference time phase (e.g., R wave) with respect to the position of the tracking point at the reference phase.

The analyzer 406a produces the time series data of the various types of motion information described above for each of the tracking points, for example. The analyzer 406a maps luminance values of colors corresponding to the values of the motion information obtained at the respective tracking points on the SR image data of the three-dimensional outline of the endocardium (or three-dimensional outline of the epicardium) of the corresponding frame, for example. As a result, the analyzer 406a produces three-dimensional analysis image data exemplarily illustrated in FIG. 7.

In the three-dimensional analysis image data exemplarily illustrated in FIG. 7, the motion information at the respective positions in the cardiac muscle is color mapped on the myoendocardium and curves dividing the cardiac muscle into a plurality of segments are rendered on the epimyocardium. The curves are rendered by the analyzer 406a based on a 17-segment model advocated by the American Heart Association (AHA), for example. In the 17-segment model, the cardiac muscle (heart wall) of the left ventricle is divided into 17 segments on the basis of anatomical positions.

At the time when setting the multiple tracking points in the first frame as illustrated on the left in FIG. 6, the analyzer 406a acquires the longitudinal direction, the short axis direction, and the positions of the cardiac apex and the cardiac base of the heart of the subject P. The analyzer 406a thus can divide the cardiac muscle of the left ventricle rendered in the first frame into 17 segments on the basis of the 17-segment model, and also divide the cardiac muscle of the left ventricle in each cardiac time phase into 17 segments by the 3DT processing. The curves are information useful for the operator to roughly grasp the portions of the cardiac muscle.

Figure 8:
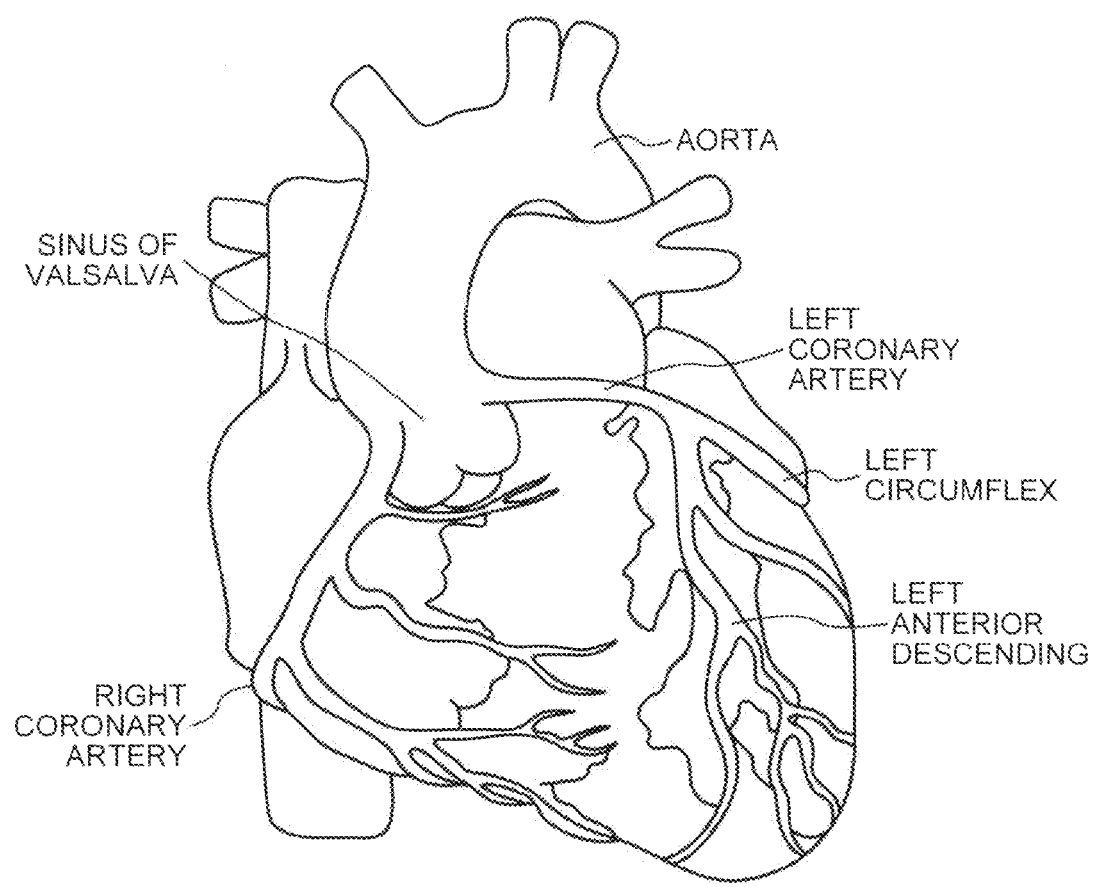
FIG. 8 is a first schematic diagram to explain an extraction unit.
Figure 9:
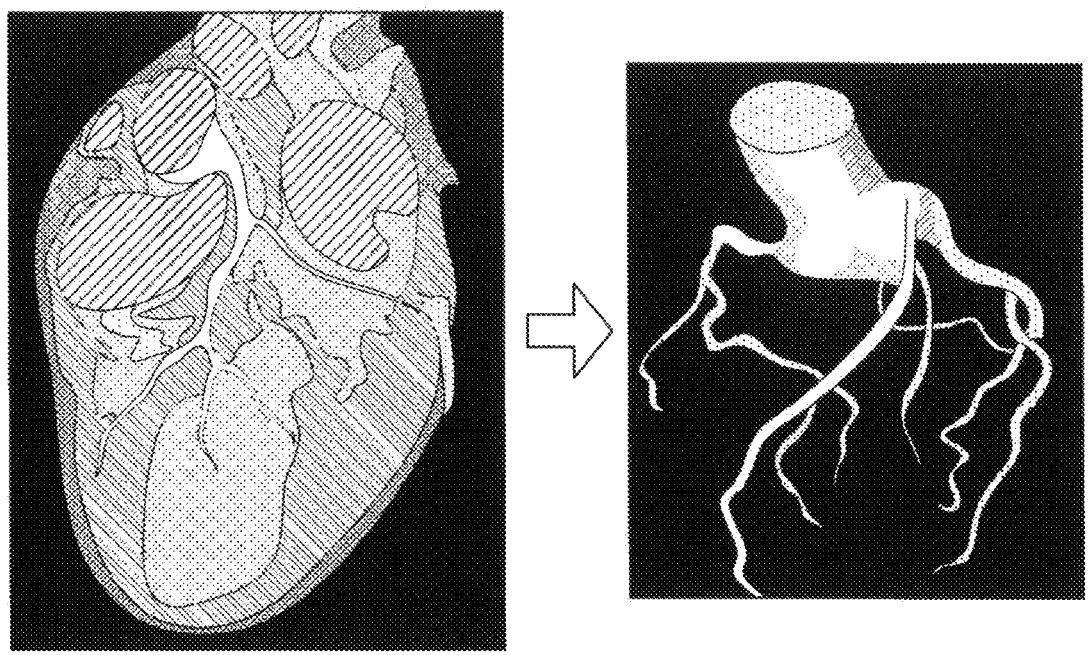
FIG. 9 is a second schematic diagram to explain the extraction unit.

The extraction unit 406b performs the processing before, after, or in parallel with the analysis processing by the analyzer 406a. The extraction unit 406b acquires the X-ray CT volume data in the arterial phase and in the diastolic phase, which data is obtained by contrast enhanced CT scan, for example, from the storage 404 and performs the segmentation processing on the acquired X-ray CT volume data to extract the region of the coronary arteries. FIGS. 8 and 9 are schematic diagrams to explain the extraction unit.

The coronary arteries are arteries that supply bloodstream (oxygen) to the cardiac muscle. As illustrated in FIG. 8, the coronary arteries repeat branching from the sinus of Valsalva of the aorta and run on the surface of the heart such that the coronary arteries surround the heart. As illustrated in FIG. 8, the coronary arteries include a right coronary artery (RCA) and a left coronary artery (LC), which branch from the sinus of Valsalva. The left coronary artery further branches into a left circumflex (LCX) and a left anterior descending (LAD). The AHA classifies the coronary arteries into a plurality of portions on the basis of the anatomical positions. The portions of the coronary arteries dominating the respective 17 segments of the cardiac muscle are roughly mapped.

The diagram on the left in FIG. 9 illustrates the X-ray CT volume data in the arterial phase and in the diastolic phase, which data is obtained by the contrast enhanced CT scan. The extraction unit 406b performs the segmentation processing on the X-ray CT volume data illustrated on the left in FIG. 9 to extract the coronary arteries. The controller 405 causes the extraction unit 406b to produce a plurality of pieces of MPR image data of the cross sections of the X-ray CT volume data illustrated on the left in FIG. 9 cut in a plurality of directions, and causes the display unit 402 to display the produced data. For example, the extraction unit 406b produces the MPR image data of the multiple cross sections including the MPR image data of two cross sections corresponding to the four-chamber cross section and the two-chamber cross section from the X-ray volume data illustrated on the left in FIG. 9.

The operator refers to the respective pieces of MPR image data and sets a seed point at a position corresponding to the sinus of Valsalva or the coronary artery such as, RCA, LC, LCX, or LAD. The extraction unit 406b performs a region-growing technique in which the voxel value of the seed point is set to a threshold and a region that has a voxel value larger than the threshold and is connected to the seed point is expanded, for example. As a result, the extraction unit 406b extracts the coronary artery volume data as exemplarily illustrated on the right in FIG. 9.

When setting the seed point, the operator may set the outline of the endocardium and the outline of epicardium by tracing the positions of the endocardium of the left ventricle and the epimyocardium in the respective pieces of MPR image data displayed on the display unit 402. Such setting operation makes it possible for the extraction unit 406b to structure a three-dimensional outline of the endocardium and a three-dimensional outline of the epimyocardium from the designated outlines of the endocardium and the epimyocardium. Furthermore, the extraction unit 406b can acquire the longitudinal direction, the short axis direction, and the positions of the cardiac apex and the cardiac base of the heart of the subject P from the three-dimensional outline of the endocardium and the three-dimensional outline of the epimyocardium.

As a result, the extraction unit 406b can divide the cardiac muscle of the left ventricle included in the X-ray CT volume data into 17 segments and acquire on which segments the respective portions of the coronary artery volume data run. The extraction unit 406b can also perform the 17-segment dividing processing by detecting the endocardial surface and the epicardial surface of the left ventricle included in the X-ray CT volume data using the threshold processing of the voxel value and the region-growing technique, for example.

The operator can view the three-dimensional analysis image data exemplarily illustrated in FIG. 7 from various directions on the display unit 402 by moving the observing point position. This technique, however, makes it impossible for the operator to check all motion information included in the three-dimensional analysis image data at the same time. Conventionally, a polar map is produced and displayed that can express all of the motion information included in the three-dimensional analysis image data exemplarily illustrated in FIG. 7 in one piece of image data, for example. FIGS. 10 to 13 are schematic diagrams to explain the polar map.

Figure 10:
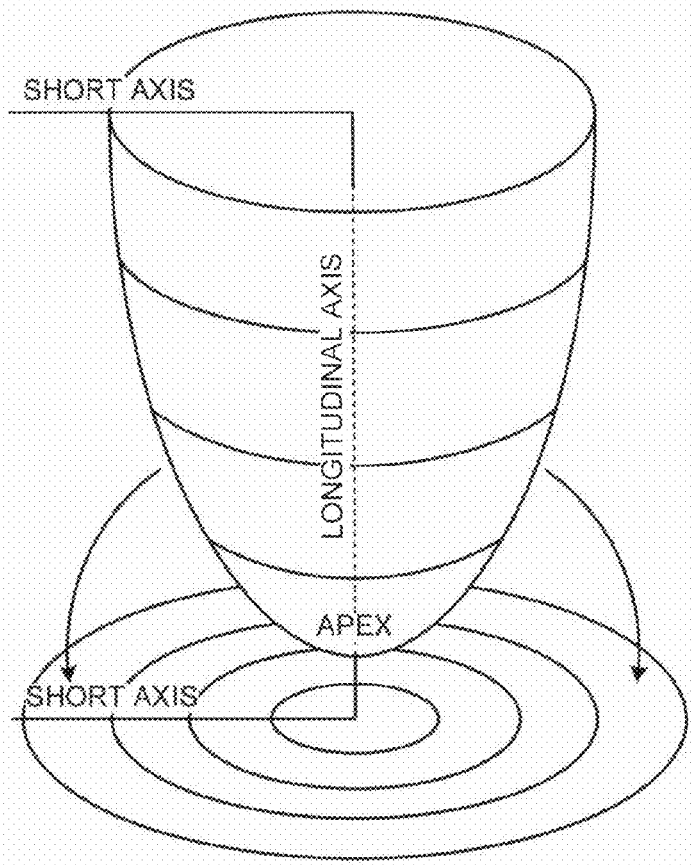
FIG. 10 is a first schematic diagram to explain a polar map.

The polar map, which is also called a "bull's eye plot", is image data obtained by developing, on a plane, three-dimensional data (e.g., three-dimensional analysis image data) in which three-dimensional heart function information is mapped. Specifically, as illustrated in FIG. 10, the polar map is image data in which the information about the three-dimensional data at each of a plurality of short-axis cross sections of the left ventricle, which sections are perpendicular to the longitudinal direction from the cardiac base where the mitral valve is located to the cardiac apex, is projected on a "circle the center of which corresponds to the cardiac apex and the periphery of which corresponds to the cardiac base". More specifically, the polar map is produced by projecting the three-dimensional data on the circle such that the respective positions in the circle indicated by two-dimensional polar coordinates (radius and angle) correspond to the respective three-dimensional positions in the cardiac muscle.

Figure 11:
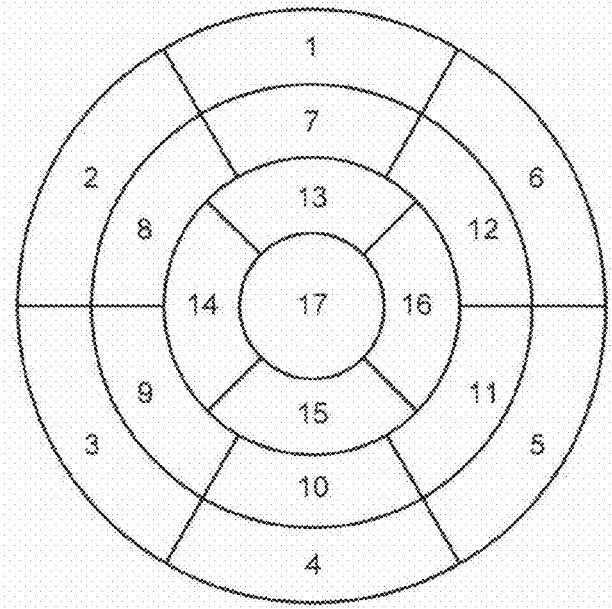
FIG. 11 is a second schematic diagram to explain the polar map.

As illustrated in FIG. 11, the circle depicted on the polar map is divided into 17 regions 1 to 17 on the basis of the 17-segment model, for example. The region 17 illustrated in FIG. 11 is the "apex", which is a region including the apex of the cardiac apex. The regions 13 to 16 illustrated in FIG. 11 are the anterior, the septel, the inferior, and the lateral at the cardiac apex level. The regions 7 to 12 illustrated in FIG. 11 are the anterior, the anteroseptal, the inferoseptal, the inferior, the inferolaterral, and the anterolateral of the cardiac muscle at the intermediate level between the cardiac apex and the cardiac base. The regions 1 to 6 illustrated in FIG. 11 are the anterior, the anteroseptal, the inferoseptal, the inferior, and the anterolateral at the cardiac base level.

Figure 12:
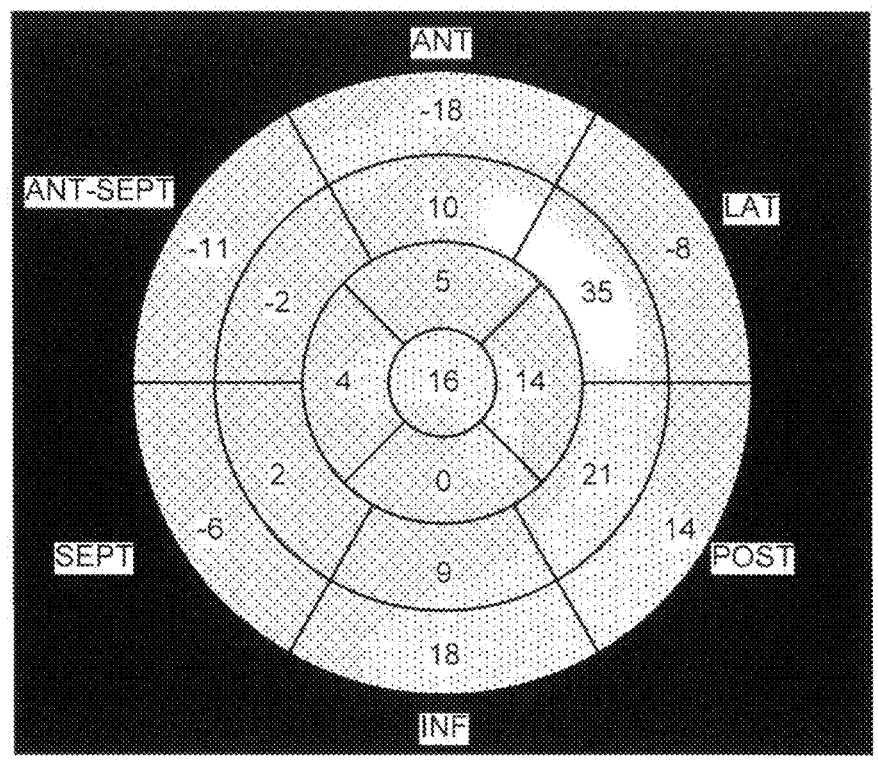
FIG. 12 is a third schematic diagram to explain the polar map.

Conventionally, the three-dimensional analysis image data exemplarily illustrated in FIG. 7 is converted into the polar map exemplarily illustrated in FIG. 12 by being projected and developed on the circle exemplarily illustrated in FIG. 11, and displayed on the display unit 402. In the polar map illustrated in FIG. 12, the values of the motion information of the three-dimensional analysis image data are color mapped on the circle. In the polar map illustrated in FIG. 12, the average values (e.g., 16, 4, 5, etc) of the pieces of motion information of the respective segments are also superimposed.

The operator can view the coronary artery volume data exemplarily illustrated on the right in FIG. 9 from various directions on the display unit 402 by moving the view observing point position. This technique, however, makes it impossible for the operator to check the whole of the three dimensional shape of the coronary arteries as is the case in the three-dimensional analysis image data. Conventionally, it is thus proposed that the coronary artery volume data exemplarily illustrated on the right in FIG. 9 is converted into the polar map exemplarily illustrated in FIG. 13 by the manner illustrated in FIG. 10 and the polar map is displayed on the display unit 402, for example.

Figure 13:
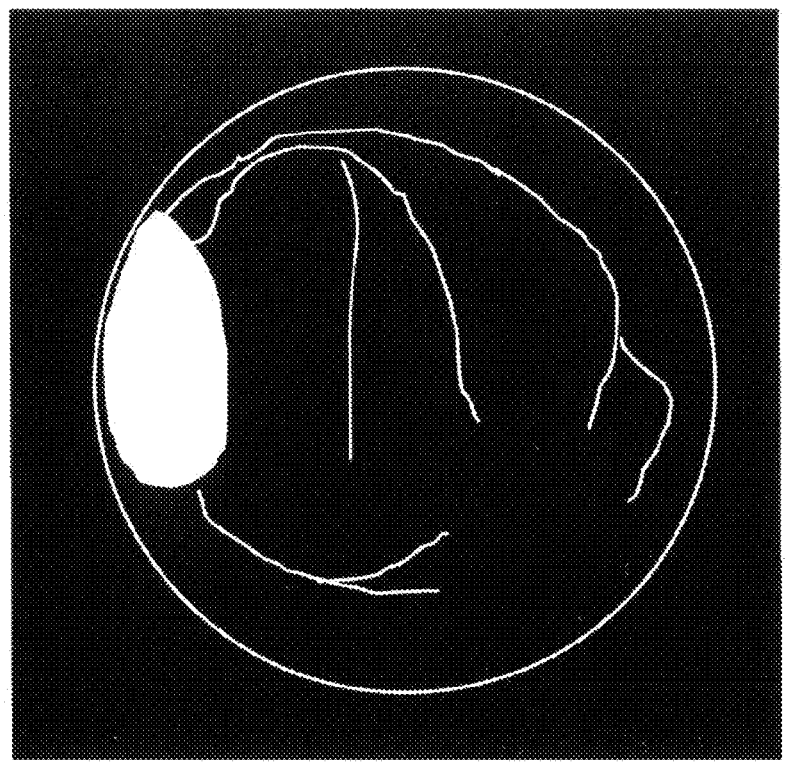
FIG. 13 is a fourth schematic diagram to explain the polar map.

In the conventional technique, a doctor needs to check the portion of the cardiac muscle where the motion function deteriorates with reference to the polar map illustrated in FIG. 12 and check the constricted portion of the coronary artery with reference to the polar map illustrated in FIG. 13. In this way, in the conventional technique, a doctor observes two polar maps separately, and reconstructs a positional relation between the portion of the cardiac muscle where the motion function deteriorates and the constricted portion of the coronary artery in the doctor's head, thereby grasping the positional relation.

In contrast, the combined image generator 406c illustrated in FIG. 4 produces the combined image data (combined polar map) by the processing described above. The development on the plane performed by the combined image generator 406c is mapping processing on a circular map (polar map) indicating a three-dimensional space in a polar coordinate system (two-dimensional polar coordinate system). The combined polar map is one piece of image data that makes it possible to observe the processing results of the analyzer 406a and the extraction unit 406b at the same time.

For example, the combined image generator 406c produces the combined polar map in which the three-dimensional analysis image data and the coronary artery volume data are developed on a surface in a state where the three-dimensional analysis image data and the coronary artery volume data are aligned. The combined image generator 406c selects the ultrasound volume data in the diastolic phase out of the ultrasound volume data group as the target volume data. The combined image generator 406c aligns the target volume data with the X-ray CT volume data in the diastolic phase. In other words, the combined image generator 406c performs the alignment such that the nourishing blood vessels (coronary arteries) rendered in the X-ray CT volume data in the diastolic phase come into contact with the surface of the heart rendered in the target volume data. The combined image generator 406c then produces the combined polar map on the basis of the alignment result.

Specifically, the combined image generator 406c according to the first embodiment combines first image data (a first polar map) of the three-dimensional heart function information (three-dimensional analysis image data) developed on a surface and second image data (a second polar map) of the three-dimensional shape (coronary artery volume data) developed on the surface on the basis of the alignment result. For example, the combined image generator 406c according to the first embodiment combines the first image data of the three-dimensional analysis image data developed on a plane and the second image data of the coronary artery volume data developed on the plane on the basis of the alignment result. As a result, the combined image generator 406c according to the first embodiment produces the combined polar map (combined image data). The combined image generator 406c according to the first embodiment may develop the three-dimensional analysis image data and the coronary artery volume data on an uneven surface.

Figure 14:
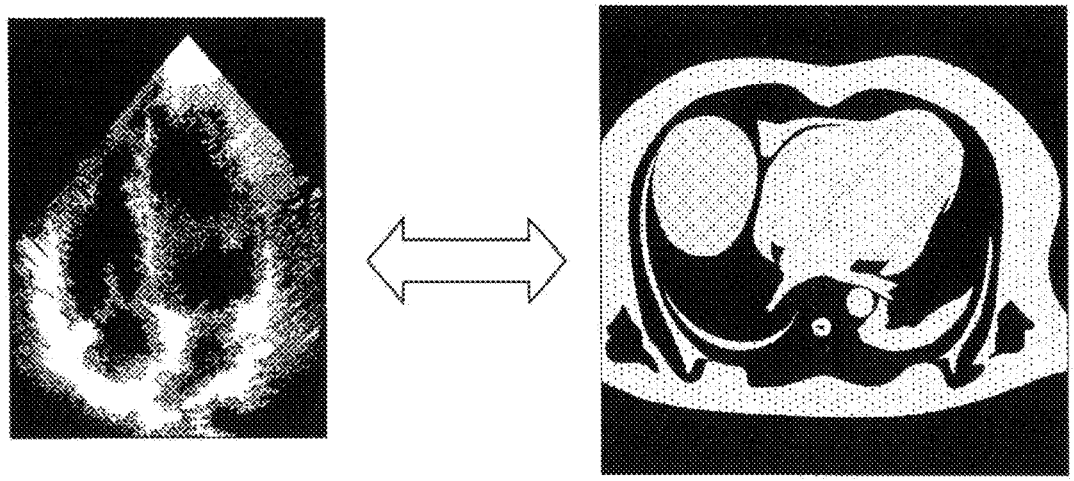
FIG. 14 is a first schematic diagram to explain a combined image generator according to the first embodiment.
Figure 15:
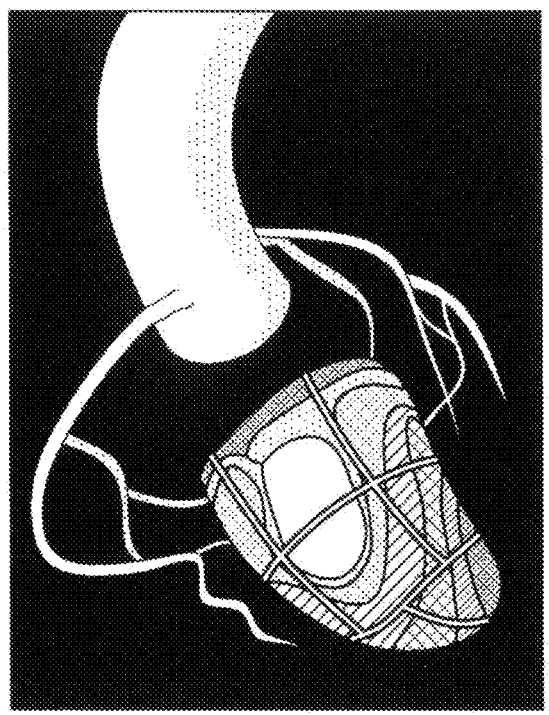
FIG. 15 is a second schematic diagram to explain the combined image generator according to the first embodiment.
Figure 16:
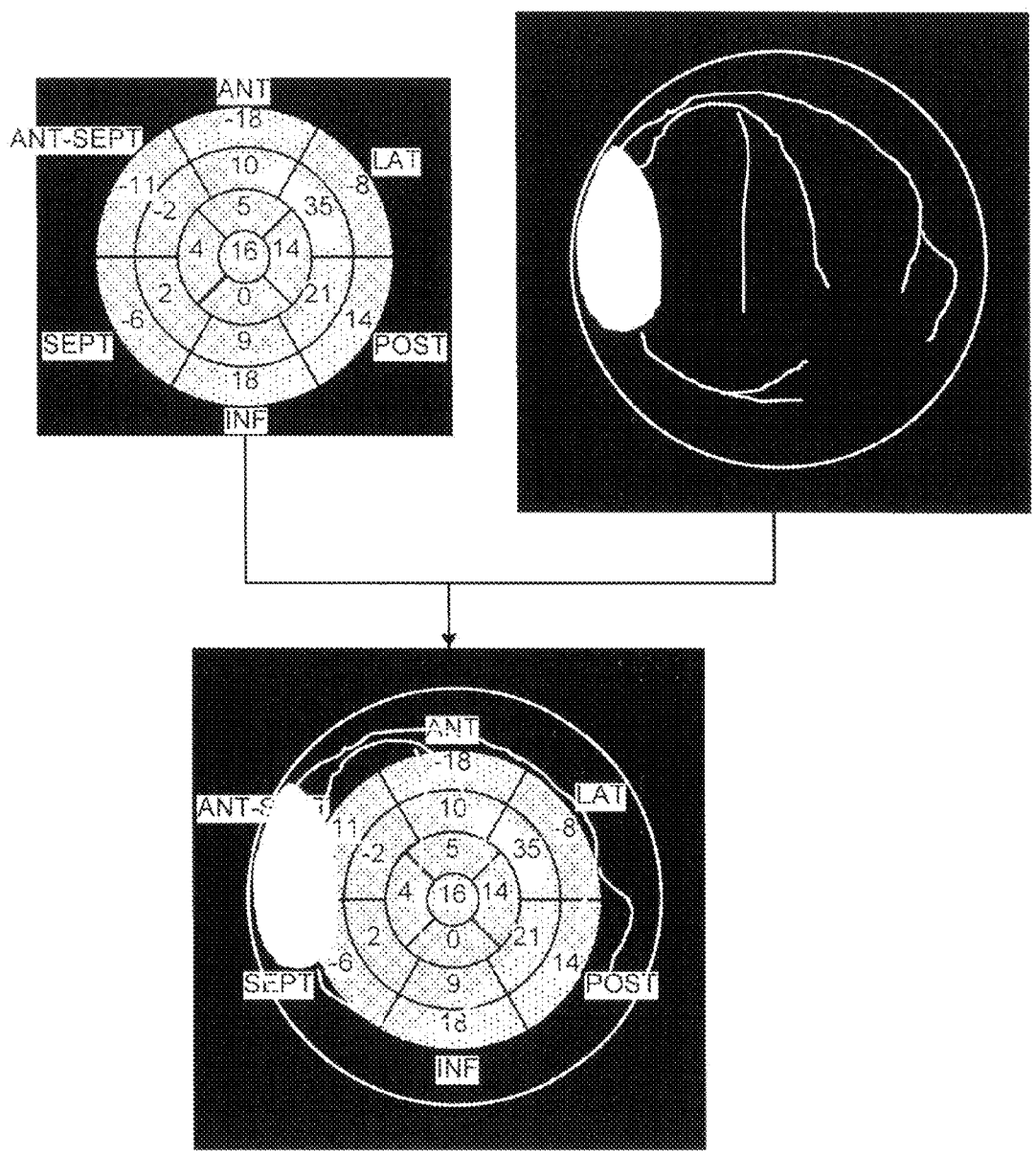
FIG. 16 is a third schematic diagram to explain the combined image generator according to the first embodiment.

FIGS. 14 to 16 are schematic diagrams to explain the combined image generator according to the first embodiment. The combined image generator 406c acquires the longitudinal direction, the short axis direction, the positions of the apex and the base of the heart of the subject P in the target volume data from the results of the 3DT processing by the analyzer 406a, for example. The combined image generator 406c also acquires the longitudinal direction, the short axis direction, the positions of the apex and the base of the heart of the subject P in the X-ray CT volume data acquired by the extraction unit 406b in accordance with the setting operation of the operator.

As illustrated in FIG. 14, on the basis of the information described above, the combined image generator 406c aligns the MPR image data corresponding to the four-chamber cross section of the target volume data with the MPR image data corresponding to the four-chamber cross section of the coronary artery volume data. In addition, the combined image generator 406c performs the alignment of various cross sections such as the alignment of the MPR image data corresponding to the two-chamber cross section of the target volume data with the MPR image data corresponding to the two-chamber cross section of the coronary artery volume data. As a result, the combined image generator 406c completes the alignment of the target volume data with the X-ray CT volume data in the diastolic phase.

In the embodiment, the alignment processing may be performed by the following manners. For example, the operator refers to the MPR image data of the various cross sections of the target volume data and the MPR image data of the various cross sections of the coronary artery volume data, and designates a plurality of anatomical feature points corresponding to each other. The combined image generator 406c aligns the target volume data with the X-ray CT volume data in the diastolic phase using such setting information.

In the alignment, the combined image generator 406c calculates a conversion matrix for converting the three-dimensional coordinate system of the coronary artery volume so as to coincide with the three-dimensional coordinate system of the three-dimensional analysis image data group of the respective cardiac time phases. The combined image generator 406c then performs image transformation processing (rotational movement, parallel movement, scaling processing, etc) on the coronary artery volume data using the conversion matrix, for example. As a result, the combined image generator 406c completes the alignment of the three-dimensional analysis image data and the coronary artery volume data, as illustrated in FIG. 15. As a result of the alignment, the coronary artery volume data in the diastolic phase runs near the surface of the three-dimensional analysis image data in the diastolic phase. FIG. 15 exemplarily illustrates a result of the alignment where the three-dimensional analysis image data in the systolic phase, from which deterioration of the motion function of the cardiac muscle can be notably observed, and the coronary artery volume data in the diastolic phase are aligned in the same three-dimensional coordinate system.

The combined image generator 406c produces the first polar map from the three-dimensional analysis image data after the alignment, as illustrated on the upper left in FIG. 16. The three-dimensional analysis image data is the time series data. The combined image generator 406c thus produces the time series data of the first polar map. In such a case, the combined image generator 406c re-maps the motion information about the three-dimensional analysis image data in a cardiac time phase other than the diastolic phase on the SR image data of the endocardium (or epicardium) in the diastolic phase after the alignment on the basis of the result of the 3DT processing, thereby producing the first polar map in a cardiac time phase other than the diastolic phase.

The combined image generator 406c produces the second polar map from the coronary artery volume data after the alignment exemplarily illustrated in FIG. 15, as illustrated on the upper right in FIG. 16. As illustrated on the upper side in FIG. 16, the second polar map is scaled such that the second polar map coincides with the two-dimensional coordinate system of the first polar map as a result of the alignment.

The combined image generator 406c combines the first polar map and the second polar map, thereby producing the combined polar map as illustrated on the lower side in FIG. 16. The first polar map is the time series data. The combined image generator 406c thus produces the combined polar maps in the respective cardiac time phases. The controller 405 causes the display unit 402 to display the combined polar maps. For example, the controller 405 causes the display unit 402 to display the time series data of the combined polar maps as a moving image or as a thumbnail image. For another example, the controller 405 causes the display unit 402 to display the combined polar map in a cardiac time phase designated by the operator.

In the embodiment, the combined image generator 406c may align the ultrasound volume data in the diastolic phase with the X-ray CT volume data in the diastolic phase by a known technique such as a cross correlation method, for example. In the embodiment, the extraction unit 406b may extract the surface of a heart from the ultrasound volume data in the diastolic phase and the surface of the heart from the X-ray CT volume data in the diastolic phase, and perform the alignment of the two extracted regions by a known technique such as the cross correlation method.

In the embodiment, the first polar map and the second polar map may be produced before the alignment, and the first polar map and the second polar map may be scaled on the basis of the alignment result to produce the combined polar map. As described above, the alignment is performed using the data in the diastolic phase. In the embodiment, any cardiac time phase can be selected as long as the cardiac time phase of the ultrasound volume data to be subjected to the alignment is substantially the same time phase as the X-ray CT volume data.

Figure 17:
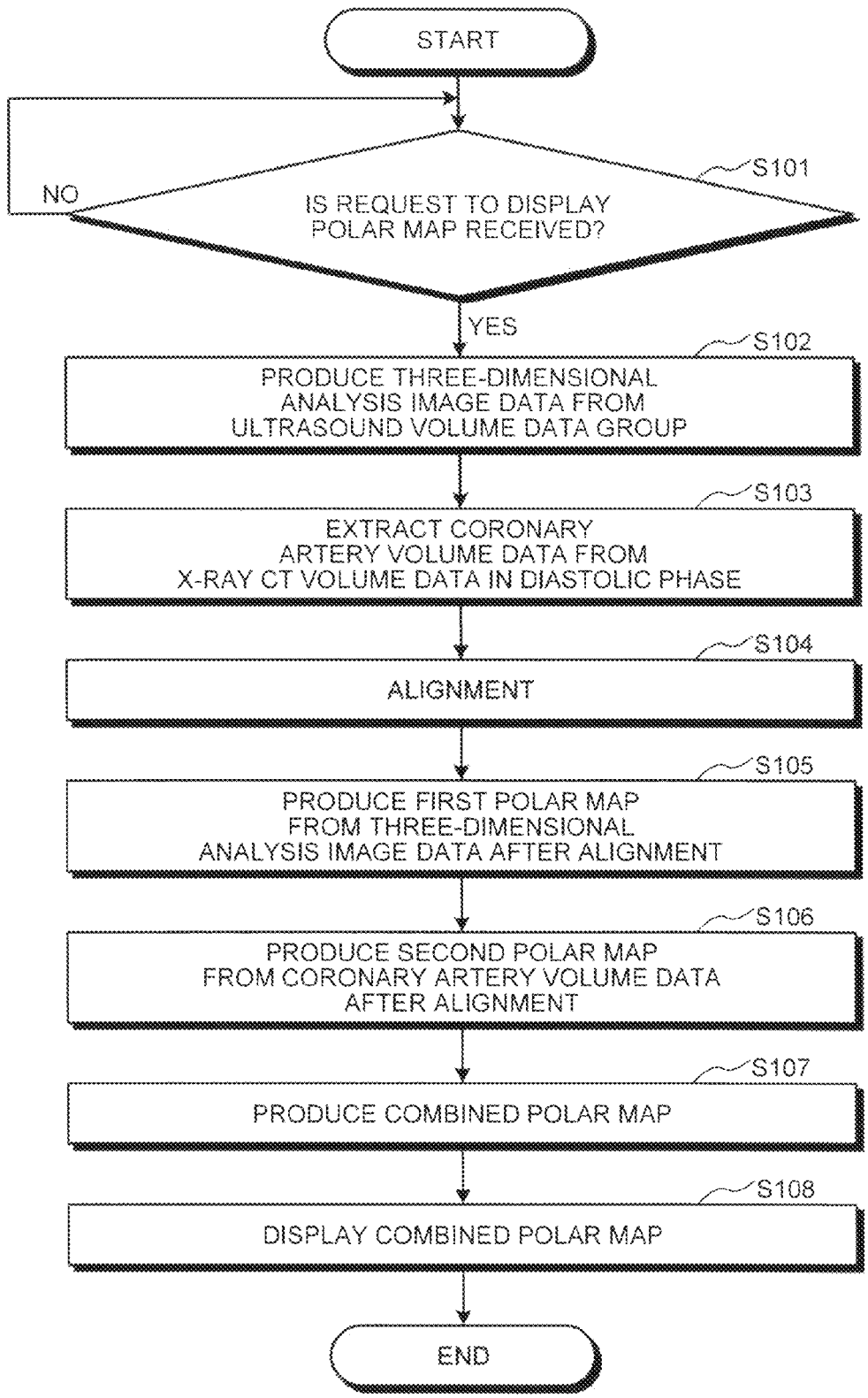
FIG. 17 is a flowchart to explain an example of the processing performed by the image processing apparatus according to the first embodiment.

The following describes a flow of the processing performed by the image processing apparatus 400 according to the first embodiment with reference to FIG. 17. FIG. 17 is a flowchart to explain an example of the processing performed by the image processing apparatus according to the first embodiment. FIG. 17 illustrates an example of the processing performed after the ultrasound volume data group and the X-ray CT volume data are stored in the storage 404.

As exemplarily illustrated in FIG. 17, the controller 405 of the image processing apparatus 400 according to the first embodiment determines whether a request to display the polar map is received (step S101). If no display request is received (No at step S101), the controller 405 waits until the reception of the display request.

If the display request is received (Yes at step S101), the analyzer 406a produces the three-dimensional analysis image data from the ultrasound volume data (step S102). The extraction unit 406b extracts the coronary artery volume data from the X-ray CT volume data in the diastolic phase (step S103).

The combined image generator 406c aligns the ultrasound volume data in the diastolic phase (target volume data) with the X-ray CT volume data (step S104). The combined image generator 406c produces the first polar map from the three-dimensional analysis image data after the alignment (step S105) and produces the second polar map from the coronary artery volume data after the alignment (step S106). The combined image generator 406c combines the first polar map and the second polar map to produce the combined polar map (step S107).

The display unit 402 displays the combined polar map under the control of the controller 405 (step S108), and thereafter the processing ends.

As described above, in the first embodiment, the combined polar map is produced and displayed in which the first polar map based on the alignment and the second polar map based on the alignment are combined. The first polar map is a polar map of the three-dimensional motion information about the left ventricle obtained from the result of the tracking processing performed on the ultrasound volume data group. This polar map thus makes it possible for the operator who performs an image diagnosis to grasp the anatomical position of a portion of the cardiac muscle where abnormal heart wall motion occurs by referring to the motion information in the combined polar map divided into 17 segments, for example.

The second polar map is a polar map of the three-dimensional form information about the whole blood vessels including the coronary arteries obtained from the result of the segmentation processing performed on the X-ray CT volume data. The combined polar map thus render the almost whole shape of the coronary arteries that repeat branching from the origin (sinus of Valsalva), thereby making it possible for the operator who performs the image diagnosis to grasp the anatomical position of a portion of the coronary artery where the constriction or the obstruction occurs.

Referring to one piece of the combined polar map, the operator who performs the image diagnosis can observe a portion of the cardiac muscle where the motion function deteriorates and a portion, which is near the portion of the cardiac muscle, of the coronary arteries where the constriction or the obstruction occurs at the same time while grasping the mutual anatomical positions, for example. The first embodiment makes it possible to readily grasp a positional relation between a portion where the heart function deteriorates and a portion causing the deterioration of the heart function.

In the first embodiment, for example, when the operator who refers to the combined polar map illustrated on the lower side in FIG. 16 designates a portion where a heart function deteriorates and a portion causing the deterioration of the heart function with a mouse, the controller 405 may display marks at the positions corresponding to the two portions on the rendering image data after the alignment illustrated in FIG. 15.

In the first embodiment, the three-dimensional analysis image data and the coronary artery volume data are combined on the basis of the alignment result. The embodiment is not limited thereto. For example, the alignment processing may be omitted when the three-dimensional analysis image data and the coronary artery volume data that are already aligned are used.

Second Embodiment

In the first embodiment, two polar maps are combined that are produced on the basis of the alignment result. One of the maps is produced from the three-dimensional heart function information and the other one is produced from the three-dimensional shape information. In a second embodiment, the combined polar map is produced from the combined data of the three-dimensional heart function information and the three-dimensional shape information.

The image processing apparatus 400 according to the second embodiment has the same structure as the image processing apparatus 400 according to the first embodiment described with reference to FIG. 4. The image processing apparatus 400 according to the second embodiment performs the 3DT processing, the segmentation processing, and the alignment processing in the same manner as the first embodiment. In the second embodiment, however, the processing performed by the combined image generator 406c differs from that in the first embodiment. The different points are mainly described below. The description of the first embodiment is also applicable to the second embodiment except for the generation method of the combined polar map.

The combined image generator 406c according to the second embodiment performs the alignment processing as described in the first embodiment. The combined image generator 406c according to the second embodiment projects, on the three-dimensional data indicating the three-dimensional heart function information (three-dimensional motion information) obtained from the first volume data group obtained by imaging the heart of the subject, the three-dimensional shape of the nourishing blood vessels of the cardiac muscle (coronary artery volume data in the diastolic phase) included in the second volume data obtained by imaging the heart, thereby producing the three-dimensional combined data. The combined image generator 406c produces the three-dimensional combined data by extrapolating a three-dimensional virtual region to the image data obtained by performing mapping on one out of the first volume data group.

For example, the combined image generator 406c according to the second embodiment projects the three-dimensional shape (coronary artery volume data in the diastolic phase) on the three-dimensional data in which the three-dimensional heart function information (three-dimensional motion information) is mapped on the endocardial surface or the epicardial surface included in the target volume data on the basis of the alignment result, thereby producing the three-dimensional combined data.

Specifically, the combined image generator 406c projects the three-dimensional shape (coronary artery volume data in the diastolic phase) on the data in which the three-dimensional virtual region is extrapolated to the three-dimensional data, thereby producing the three-dimensional combined data. In the embodiment, a three-dimensional virtual surface is extrapolated to the three-dimensional data so as to form the three-dimensional virtual region. More specifically, the combined image generator 406c calculates a regression plane at the cardiac base level of the three-dimensional data and sets new outline constituting points at positions apart from the respective outline constituting points constituting the regression plane with a constant distance, thereby extrapolating the three-dimensional virtual surface.

For example, the combined image generator 406c extrapolates the three-dimensional virtual region until the three-dimensional shape is projected on the three-dimensional combined data up to a range where the anatomical position of the nourishing blood vessels (coronary arteries) can be identified. For example, the combined image generator 406c extrapolates the three-dimensional virtual surface until the origin (sinus of Valsalva) of the nourishing blood vessels (coronary arteries) is projected on the three-dimensional combined data.

Figure 18:
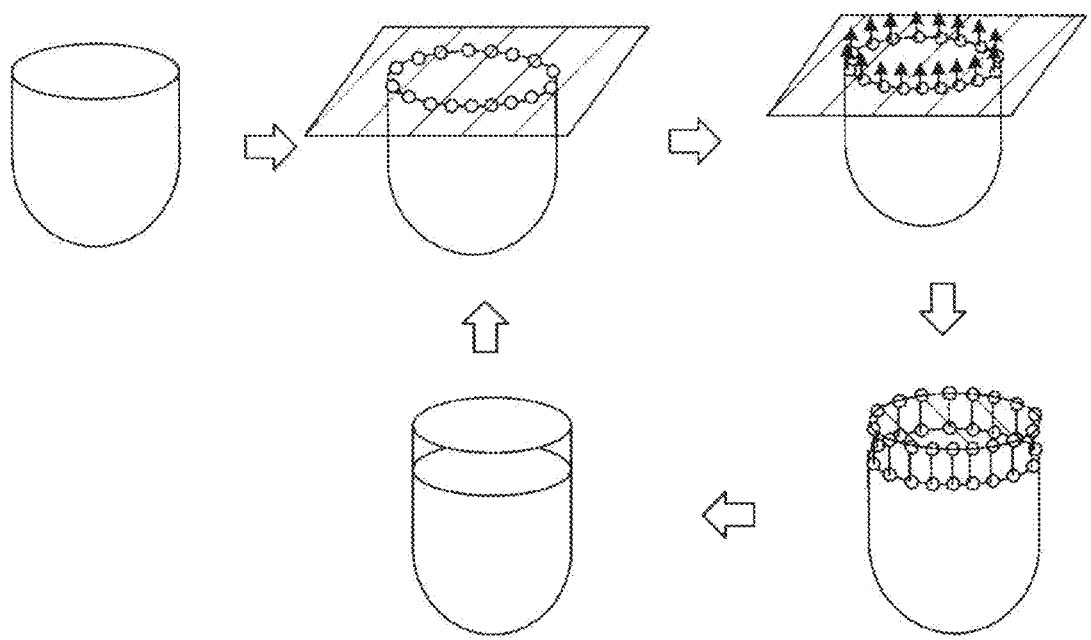
FIG. 18 is a first schematic diagram to explain the combined image generator according to a second embodiment.
Figure 19:
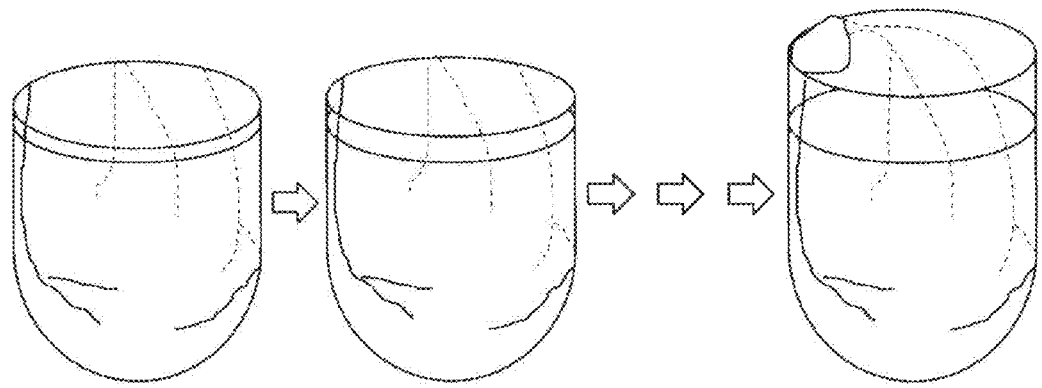
FIG. 19 is a second schematic diagram to explain the combined image generator according to the second embodiment.
Figure 20:
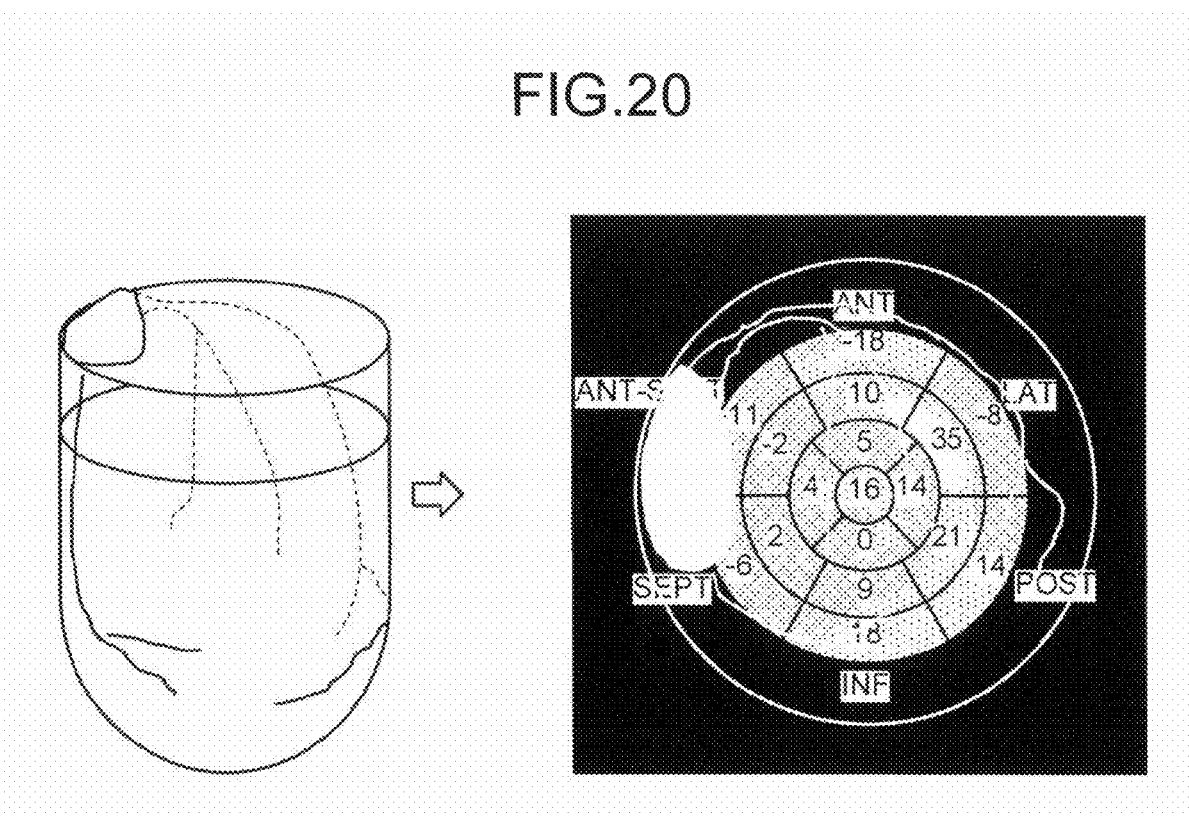
FIG. 20 is a third schematic diagram to explain the combined image generator according to the second embodiment.

The combined image generator 406c according to the second embodiment produces the combined image data (combined polar map) by developing the three-dimensional combined data on a surface. For example, the combined image generator 406c according to the second embodiment produces the combined image data by developing the three-dimensional combined data on a plane. The combined image generator 406c according to the second embodiment may develop the three-dimensional combined data on an uneven surface. The following describes an example of the processing described above with reference to FIGS. 18 to 20. FIGS. 18 to 20 are schematic diagrams to explain the combined image generator according to the second embodiment.

The diagram on the upper left in FIG. 18 illustrates the three-dimensional analysis image data in which the motion information at the respective positions in the cardiac muscle in a certain cardiac time phase is mapped on the SR image data of the endocardium produced from the ultrasound volume data (target volume data) in the diastolic phase. The three-dimensional analysis image data is disposed in the three-dimensional coordinate system after the alignment.

The three-dimensional analysis image data renders the motion information from the cardiac base to the cardiac apex of the left ventricle. The coronary artery volume data obtained by the segmentation processing, which differs from the three-dimensional analysis image data obtained by the ultrasound scanning, includes the "form information about the aorta, and coronary arteries from the origin to the ends", for example, besides the left ventricle. In the second embodiment, the three-dimensional combined data is produced in which the three-dimensional analysis image data and the coronary artery volume data are combined. It is, however, difficult to project all of the coronary artery volume data having the three-dimensional form information about the coronary arteries widely covering the portions including the left ventricle on the three-dimensional analysis image data having the motion information about only the left ventricle.

The combined image generator 406c according to the second embodiment thus extrapolates the three-dimensional virtual surface to the three-dimensional analysis image data illustrated on the upper left in FIG. 18 so as to form the three-dimensional virtual region from the cardiac base toward the atrium. Specifically, as illustrated on the upper middle in FIG. 18, the combined image generator 406c calculates the regression plane (refer to the rectangle hatched with the oblique lines in FIG. 18) from the outline constituting points (refer to the outlined circles in FIG. 18) constituting the cardiac base level in the three-dimensional analysis image data.

As illustrated on the upper right in FIG. 18, the combined image generator 406c calculates the positions apart from the respective outline constituting points with a constant distance (the ends of the respective arrows in FIG. 18) perpendicular to the calculated regression plane. As a result, as illustrated on the lower right in FIG. 18, the combined image generator 406c newly defines the outline constituting points and the plane constituted by the newly defined outline constituting points. In this way, as illustrated on the lower middle in FIG. 18, the combined image generator 406c extrapolates the three-dimensional virtual surface so as to form the three-dimensional virtual region.

The combined image generator 406c repeats the processing described above, thereby sequentially extrapolating the three-dimensional virtual regions from the cardiac base of the left ventricle towards the atrium. The combined image generator 406c projects the coronary artery volume data perpendicularly onto the surface of the three-dimensional analysis image data after the extrapolation. As a result, the three-dimensional combined data is produced in which the coronary artery volume data comes into contact with the surface of the three-dimensional analysis image data.

The number of repeats of the extrapolation processing with a constant distance is preliminarily set on the basis of the typical distance from the cardiac base to the sinus of Valsalva, for example. Alternatively, in order to perform the extrapolation processing one time, the constant distance may be set to N times (e.g., 1.5 times) of the distance from the cardiac apex to the cardiac base such that the ends of the coronary arteries to the sinus of Valsalva in the coronary artery volume data can be projected.

The extrapolation processing is preferably repeated until the operator determines that the operator can identify the anatomical positions of the coronary arteries. For example, as illustrated in FIG. 19, the combined image generator 406c produces the three-dimensional combined data and the VR image data of the three-dimensional combined data for each extrapolation processing under the control of the controller 405. The display unit 402 displays the VR image data. The operator determines whether the coronary arteries are projected on the three-dimensional combined data up to a range where the operator can identify the anatomical positions of the coronary arteries, with reference to the VR image data from the various observing point positions. For example, the operator instructs the end of the extrapolation processing when the VR image data is displayed in which the coronary arteries from the ends to the sinus of Valsalva are displayed as illustrated on the right in FIG. 19.

As illustrated in FIG. 20, the combined image generator 406c produces the combined polar map from the three-dimensional combined data at the time when the operator instructs the end of the extrapolation processing. The display unit 402 then displays the combined polar map. When the operator determines the number of repeats of the extrapolation processing, the controller 405 may produce and display the combined polar map for each extrapolation processing. As described in the first embodiment, the motion information is the time series data. The combined polar map is thus produced as the time series data in the second embodiment, too.

Figure 21:
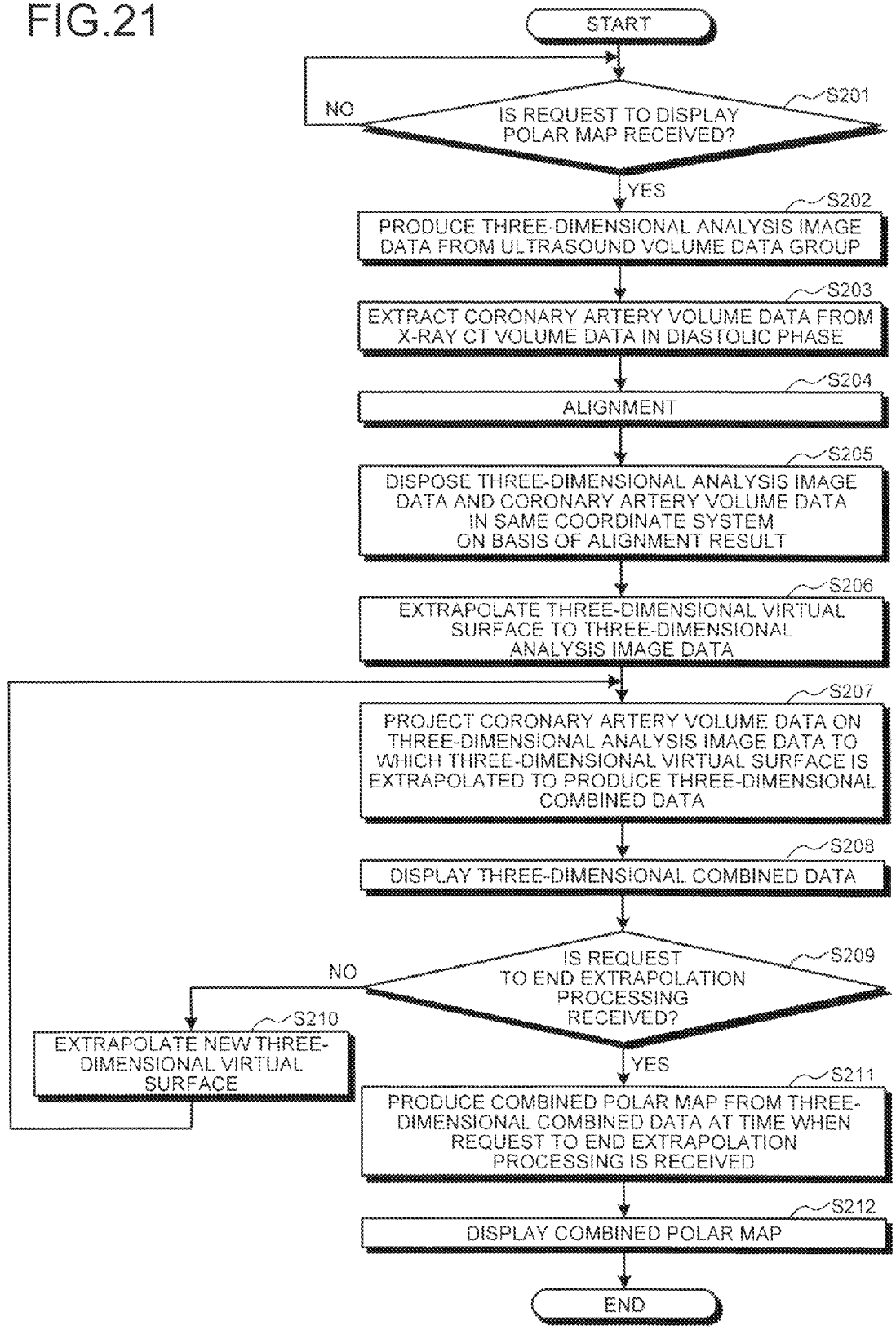
FIG. 21 is a flowchart to explain an example of the processing performed by the image processing apparatus according to the second embodiment.

The following describes a flow of the processing performed by the image processing apparatus 400 according to the second embodiment with reference to FIG. 21. FIG. 21 is a flowchart to explain an example of the processing performed by the image processing apparatus according to the second embodiment. FIG. 21 illustrates an example of the processing performed after the ultrasound volume data group and the X-ray CT volume data are stored in the storage 404.

As exemplarily illustrated in FIG. 21, the controller 405 of the image processing apparatus 400 according to the second embodiment determines whether a request to display the polar map is received (step S201). If no display request is received (No at step S201), the controller 405 waits until the reception of the display request.

If the display request is received (Yes at step S201), the analyzer 406a produces the three-dimensional analysis image data from the ultrasound volume data group (step S202). The extraction unit 406b extracts the coronary artery volume data from the X-ray CT volume data in the diastolic phase (step S203).

The combined image generator 406c aligns the ultrasound volume data in the diastolic phase (target volume data) with the X-ray CT volume data (step S204). The combined image generator 406c disposes the three-dimensional analysis image data and the coronary artery volume data in the same coordinate system on the basis of the alignment result (step S205).

The combined image generator 406c extrapolates the three-dimensional virtual surface to the three-dimensional analysis image data (step S206), and projects the coronary artery volume data on the three-dimensional analysis image data having the extrapolated three-dimensional virtual surface, thereby producing the three-dimensional combined data (step S207). The display unit 402 displays the three-dimensional combined data (the VR image data of the three-dimensional combined data) (step S208).

The controller 405 determines whether a request to end the extrapolation processing is received (step S209). If no extrapolation end request is received (No at step S209), the combined image generator 406c extrapolates a new three-dimensional virtual surface by the instruction from the controller 405 (step S210). The processing returns to step S207, where the processing is performed to produce new three-dimensional combined data.

If the extrapolation end request is received (Yes at step S209), the combined image generator 406c produces the combined polar map from the three-dimensional combined data at the time when the extrapolation end request is received (step S211). The display unit 402 displays the combined polar map under the control of the controller 405 (step S212), and thereafter the processing ends.

As described above in the second embodiment, the combined polar map is produced and displayed from the three-dimensional combined data in which the form information about the coronary arteries is projected on the endocardial surface or the epicardial surface on which the motion information is mapped in the state where the ultrasound volume data and the X-ray CT volume data are aligned. In other words, in the second embodiment, the combined polar map is produced and displayed while the form of the coronary arteries comes into contact with the endocardial surface, for example. The second embodiment thus makes it possible to accurately and readily grasp a positional relation between a portion where the heart function deteriorates and a portion causing the deterioration of the heart function.

In the second embodiment, the three-dimensional virtual surface is extrapolated to the three-dimensional data so as to form the three-dimensional virtual region. The second embodiment is not limited thereto. For example, a circular cylinder may be extrapolated to the three-dimensional data as the three-dimensional virtual region. In such a case, the combined image generator 406c extrapolates, to the regression plane at the cardiac base level in the three-dimensional data, a circular cylinder having the bottom surface of the same plane as the regression plane and a certain height as the three-dimensional virtual region, for example. The combined image generator 406c projects the three-dimensional shape on the data to which the circular cylinder is extrapolated as the three-dimensional virtual region, thereby producing the three-dimensional combined data.

In the second embodiment, the three-dimensional combined data is produced by projecting the coronary artery volume data in the diastolic phase on the three-dimensional data on which the motion information is mapped on the basis of the alignment result. The embodiment is not limited thereto. For example, the alignment processing may be omitted when the three-dimensional analysis data on which the aligned three-dimensional motion information is already mapped and the coronary artery volume data in the diastolic phase are used.

The image processing methods described in the first and the second embodiments may be applied to a case where the coronary artery volume data is extracted from the MRI volume data. The image processing methods described in the first and the second embodiments may be performed by any one of the ultrasound diagnosis apparatus 100, the X-ray CT apparatus 200, and the image processing apparatus 400, and may be performed among them in cooperation with one another. That is, specific forms of distributions and integrations of the respective processors described in the first and the second embodiments are not limited to those illustrated in the drawings. All or part of the processors can be configured to be functionally or physically distributed or integrated in arbitrary units in accordance with various loads, the usage states, and the like.

The image processing methods described in the first and the second embodiments can be achieved by a computer such as a personal computer or a work station executing a preliminarily prepared image processing program. The image processing program can be distributed through a network such as the Internet. The image processing program can be recorded on a computer readable recording medium such as a hard disk, a flexible disk (FD), a compact disc read only memory (CD-ROM), a magnetooptic (MO) disc, or a digital versatile disc (DVD), and read from the recording medium and executed by the computer.

As described above, the first and second embodiments make it possible to readily grasp a positional relation between a portion where the heart function deteriorates and a portion causing the deterioration of the heart function.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
a combined image generator circuit configured to produce three-dimensional combined data by projecting a three-dimensional shape of blood vessels feeding a cardia muscle onto a surface of three-dimensional data on which three-dimensional heart function information is three-dimensionally mapped, the three-dimensional data obtained from a first volume data group obtained by imaging the heart, the three-dimensional shape included in second volume data obtained by imaging the heart, and produce a polar map in which the three-dimensional combined data is developed on a surface; and
a controller circuit configured to cause a display to display the polar map.

2. The image processing apparatus according to claim 1, wherein the combined image generator circuit produces the three-dimensional combined data by extrapolating a three-dimensional virtual region to image data obtained by performing mapping on one out of the first volume data group.

3. The image processing apparatus according to claim 2, wherein the combined image generator circuit extrapolates the three-dimensional virtual region by calculating a regression plane at a cardiac base level in the three-dimensional data and setting new outline constituting points at positions apart from the outline constituting points constituting the regression plane with a constant distance.

4. The image processing apparatus according to claim 3, wherein the combined image generator circuit extrapolates the three-dimensional virtual region until the three-dimensional shape is projected on the three-dimensional combined data up to a range that allows anatomical positions of the blood vessels feeding the cardiac muscle to be identified.

5. The image processing apparatus according to claim 2, wherein the combined image generator circuit extrapolates the three-dimensional virtual region until the three-dimensional shape is projected on the three-dimensional combined data up to a range that allows anatomical positions of the blood vessels feeding the cardiac muscle to be identified.

6. The image processing apparatus according to claim 2, wherein the combined image generator circuit produces the polar map in a state where the three-dimensional data and the three-dimensional shape are aligned.

7. The image processing apparatus according to claim 6, wherein the combined image generator circuit aligns the second volume data and a target volume data obtained in a cardiac time phase substantially the same as a cardiac time phase when the second volume data is obtained out of the first volume data group, and produces the polar map on the basis of a result of the alignment.

8. The image processing apparatus according to claim 7, wherein the combined image generator circuit produces the three-dimensional combined data by projecting the three-dimensional shape on three-dimensional data in which the three-dimensional heart function information is mapped on an endocardial surface or an epicardial surface included in the target volume data on the basis of a result of the alignment.

9. The image processing apparatus according to claim 6, wherein
the first volume data group is an ultrasound volume data group,
the three-dimensional heart function information is local motion information about the cardiac muscle obtained by tracking processing using the ultrasound volume data group,
the second volume data is X-ray computer tomography (CT) volume data or magnetic resonance imaging (MRI) volume data, and
the three-dimensional shape is volume data of coronary arteries extracted from the X-ray CT volume data or the MRI volume data.

10. The image processing apparatus according to claim 2, wherein the development of the three-dimensional combined data on the surface performed by the combined image generator circuit is a mapping processing on a circular map indicating a three-dimensional space in a polar coordinate system.

11. The image processing apparatus according to claim 2, wherein
the first volume data group is an ultrasound volume data group,
the three-dimensional heart function information is local motion information about the cardiac muscle obtained by tracking processing using the ultrasound volume data group,
the second volume data is X-ray computer tomography (CT) volume data or magnetic resonance imaging (MRI) volume data, and the three-dimensional shape is volume data of coronary arteries extracted from the X-ray CT volume data or the MRI volume data.

12. The image processing apparatus according to claim 1, wherein the combined image generator circuit produces the polar map in a state where the three-dimensional data and the three-dimensional shape are aligned.

13. The image processing apparatus according to claim 12, wherein the combined image generator circuit aligns the second volume data and a target volume data obtained in a cardiac time phase substantially the same as a cardiac time phase when the second volume data is obtained out of the first volume data group, and produces the polar map on the basis of a result of the alignment.

14. The image processing apparatus according to claim 13, wherein the combined image generator circuit produces the three-dimensional combined data by projecting the three-dimensional shape on the three-dimensional data in which the three-dimensional heart function information is mapped on an endocardial surface or an epicardial surface included in the target volume data on the basis of a result of the alignment.

15. The image processing apparatus according to claim 12, wherein
the first volume data group is an ultrasound volume data group,
the three-dimensional heart function information is local motion information about the cardiac muscle obtained by tracking processing using the ultrasound volume data group,
the second volume data is X-ray computer tomography (CT) volume data or magnetic resonance imaging (MRI) volume data, and
the three-dimensional shape is volume data of coronary arteries extracted from the X-ray CT volume data or the MRI volume data.

16. The image processing apparatus according to claim 1, wherein the development of the three-dimensional combined data on the surface performed by the combined image generator circuit is mapping processing on a circular map indicating a three-dimensional space in a polar coordinate system.

17. The image processing apparatus according to claim 1, wherein
the first volume data group is an ultrasound volume data group,
the three-dimensional heart function information is local motion information about the cardiac muscle obtained by tracking processing using the ultrasound volume data group,
the second volume data is X-ray computer tomography (CT) volume data or magnetic resonance imaging (MRI) volume data, and
the three-dimensional shape is volume data of coronary arteries extracted from the X-ray CT volume data or the MRI volume data.

18. An ultrasound diagnosis apparatus, comprising:
an image generator circuit configured to produce a first volume data group of a heart of a subject, the heart being imaged by three-dimensional scanning with ultrasound waves;
an analyzer circuit configured to produce three-dimensional heart function information by analysis processing including tracking processing using the first volume data group;
a combined image generator circuit configured to produce three-dimensional combined data by projecting a three-dimensional shape of blood vessels feeding a cardiac muscle onto a surface of three-dimensional data on which the three-dimensional heart function information is three-dimensionally mapped, the three-dimensional shape included in second volume data obtained by imaging the heart, and produce a polar map in which the three-dimensional combined data is developed on a surface; and
a controller circuit configured to cause a display to display the polar map.

19. An image processing method, comprising:
producing three-dimensional combined data by projecting a three-dimensional shape of blood vessels feeding a cardiac muscle onto a surface of three-dimensional data on which three-dimensional heart function information is three-dimensionally mapped, the three-dimensional data obtained from a first volume data group obtained by imaging the heart, the three-dimensional shape included in second volume data obtained by imaging the heart and producing a polar map in which the three-dimensional combined data is developed on a surface; and
causing a display to display the polar map.

* * * * *